US011118200B2

(12) United States Patent
Vergne-Vaxelaire et al.

(10) Patent No.: US 11,118,200 B2
(45) Date of Patent: Sep. 14, 2021

(54) METHOD FOR PREPARING AMINES FROM ALDEHYDES AND KETONES BY BIOCATALYSIS

(71) Applicants: COMMISSARIAT A L'ENERGIE ATOMIQUE ET AUX ENERGIES ALTERNATIVES, Paris (FR); UNIVERSITE D'EVRY VAL D'ESSONNE (UEVE), Evry (FR)

(72) Inventors: Carine Vergne-Vaxelaire, Cerny (FR); Véronique De Berardinis, Paris (FR); Anne Zaparucha, Bures sur Yvette (FR)

(73) Assignees: COMMISSARIAT A L'ENERGIE ATOMIQUE ET AUX ENERGIES ALTERNATIVES, Paris (FR); UNIVERSITE D'EVRY VAL D'ESSONNE (UEVE), Evry (FR)

( * ) Notice: Subject to any disclaimer, the term of this patent is extended or adjusted under 35 U.S.C. 154(b) by 0 days.

(21) Appl. No.: 16/628,688

(22) PCT Filed: Jul. 5, 2018

(86) PCT No.: PCT/EP2018/068288
§ 371 (c)(1),
(2) Date: Jan. 6, 2020

(87) PCT Pub. No.: WO2019/008110
PCT Pub. Date: Jan. 10, 2019

(65) Prior Publication Data
US 2020/0224225 A1 Jul. 16, 2020

(30) Foreign Application Priority Data
Jul. 6, 2017 (EP) .................... 17305873

(51) Int. Cl.
C12P 13/02 (2006.01)
C12P 13/00 (2006.01)
C12N 9/02 (2006.01)
C12N 9/04 (2006.01)
C12N 9/06 (2006.01)

(52) U.S. Cl.
CPC .......... *C12P 13/001* (2013.01); *C12N 9/0006* (2013.01); *C12N 9/0012* (2013.01); *C12Y 106/01* (2013.01)

(58) Field of Classification Search
CPC .. C12N 9/1096; C12N 9/0016; C12N 9/0036; C12N 9/78; C12N 9/0073; C12N 1/38; C12P 13/001; C12P 7/26; C12Y 106/01

USPC ................... 435/189, 128, 148, 252.3, 321.2
See application file for complete search history.

(56) References Cited

U.S. PATENT DOCUMENTS

2013/0309734 A1 11/2013 Bommarius et al.

OTHER PUBLICATIONS

Devos et al., Proteins: Structure, Function and Genetics, 2000, vol. 41: 98-107.*
Whisstock et al., Quarterly Reviews of Biophysics, 2003, vol. 36 (3): 307-340.*
Witkowski et al., Biochemistry, 1999. 38:11643-11650.*
Kisselev L., Structure, 2002, vol. 10: 8-9.*
Aleku, G. A. et al. "A reductive aminase from *Aspergillus oryzae*" *Nature Chemistry*, published online May 29, 2017, pp. 961-969, vol. 9, No. 10.
Database UniProt [Online] Accession No. C3UMY1, Jun. 16, 2009, p. 1, XP-002784479.
Mangas-Sanchez, J. et al. "Imine reductases (IREDs)" *Current Opinion in Chemical Biology*, 2017, pp. 19-25, vol. 37.
Maugeri, Z. et al. "Reductive amination of ketones catalyzed by whole cell biocatalysts containing imine reductases (IREDs)" *Journal of Biotechnology*, 2017, pp. 167-170, vol. 258.
Sharma, M. et al. "NAD(P)H-Dependent Dehydrogenases for the Asymmetric Reductive Amination of Ketones: Structure, Mechanism, Evolution and Application" *Adv. Synth. Catal.*, 2017, pp. 2011-2025, vol. 359, No. 12.
Database UniProt [Online] Accession No. A0A0D618P6, May 27, 2015, p. 1, XP-002776526.
Written Opinion in International Application No. PCT/EP2018/068288, dated Nov. 9, 2018, pp. 1-9.
Mayol, O. et al. "A family of native amine hydrogenases for the asymmetric reductive amination of ketones" *Nature Catalysis*, Apr. 2019, vol. 2, pp. 324-333, Supplementary Information (pp. 1-53).

* cited by examiner

Primary Examiner — Robert B Mondesi
Assistant Examiner — Mohammad Y Meah
(74) Attorney, Agent, or Firm — Saliwanchik, Lloyd & Eisenschenk

(57) ABSTRACT

The present invention relates to the preparation of amines from aldehydes and ketones by reductive amination with enzymes having a reductive aminase activity on aldehydes and ketones devoid of any carboxyl group gamma of the carbonyl group. The invention also relates to the enzymes per se and their uses in biocatalysis. The enzymes are derived from *Mycobacterium smegmatis* and vaccae, *Cystobacter fuscus*, *Microbacterium* sp. and *Aminomonas pauciv-orans*.

18 Claims, 7 Drawing Sheets
Specification includes a Sequence Listing.

|  | C3UMY1<br>SEQ ID<br>NO:3 | A0A101AWU7<br>SEQ ID NO:6 | A0A0D6I8P6<br>SEQ ID NO:1 | K0UKT5<br>SEQ ID NO:5 | S9Q235<br>SEQ ID NO:2 | E3CZE3<br>SEQ ID NO:4 |
|---|---|---|---|---|---|---|
| C3UMY1 | 100 | 63 | 66 | 65 | 38 | 38 |
| A0A101AWU7 | 63 | 100 | 75 | 75 | 37 | 38 |
| A0A0D6I8P6 | 66 | 75 | 100 | 90 | 37 | 39 |
| K0UKT5 | 65 | 75 | 90 | 100 | 37 | 38 |
| S9Q235 | 38 | 37 | 37 | 37 | 100 | 59 |
| E3CZE3 | 38 | 38 | 38 | 38 | 58 | 100 |

**SEQ ID NO:1 : Enzyme of Uniprot code A0A0D6I8P6 from *Mycobacterium smegmatis***
MSDIRAVVYGVGAMNSIVAGMLLDKGVQIVGAIARSPQKVGQDLGDLLGLGRQLGVAVSD
DAAEVLEQTHPDIAVIAVNSYLTDAVEQLRICAEHGVNAVTLSEEMLYPWETSPELSAEL
DALAKSTGATLTGTGYQDTFWVNMIALLMGTAHRIDTVRGKASWNVDDFGPELATAQQVG
RTVAEFDEWVRGAQRPPTFGRNVLDALVADTGLTVKSITTATRPDIASAAMRSEALGIDL
APGDVIGFTDIDRIETEEGPVFEFEMSGRVYGPGEGDINEWTIEGEPNLFLSNGTVPTQT
TTCTQMVNRIPDVIAAPPGIVTVDRLPRLRYRPQF

**SEQ ID NO:2 : Enzyme of Uniprot code S9Q235 from *Cystobacter fuscus* DSM 2262**
MSKRPIRIIQWGCGLMGQTLIRTLREKGAELVGAIDHNAARRDRDAGEVAGLGQSLGVRI
HPPDQADAVFREARADVCILCTRSIMSELAGALRVAARHGVNAITIGEEAFYPWTTSQAL
TEELDQLARANDCTLTGSGFQDVFWGNLITVLAGATHRIDRIVGLTQYNADDYGSALAQK
HGVGLDPETFAARIGASNSPSYVWNSNEWLCAQLGWRVRDIRQQLLPTTHTGTLRSASLG
REVPAGHATGMKAVVVTETHEGPVIETHCVGKLYAPGEVDLNEWTLRGEPDTTVTIRQPA
TPALTCATVLNRLPQLLAAPPGFVTTDRFTPATYVSRLETEA

**SEQ ID NO:3 : Enzyme of Uniprot code C3UMY1 from *Microbacterium* sp. MA1**
MTNIRAVVYGVGAMNSVITRYLLDKDVEIVGAISRSPDKVGKDLGEVTGLDRRLGVSISD
DPHEVFTRTSPDIAVVAITSYLVDAAEHFRIALSHGVNVITLSEEALYPWNTAPELTAEL
DALAKEHGVTITGGGFQDSFWVNAVAQLMGTAHRIDSVTGTSSWNVDEYGPELAELQQVG
ATIEEFDAWCREAVRPPTFGRIALDALVAGAGLTPKQILTRTEPELAHETLHCAALGIDV
PPGKCIGFTDIDEIRTEEGPVFVFRMSGRLYGPDDSDVNEWTIHGEPDLVMSNGTPPTMA
TTCTQLVNRIPDVLDADPGFVTVVDLPRLRYRHGRLHDHLSRWSSDRYIVREEL

**SEQ ID NO:4 : Enzyme of Uniprot code E3CZE3 from *Aminomonas paucivorans* DSM 12260**
MEKIRVIQYGCGKMGKVFLRYLHEKGAEIVGAIDGNPELEGKDAGEVAGLGFKLNVPVHT
DADSVFESCDADACIIAVASLMEDMLPHLERAARYGVNAITTCEEAFYPWTTSPAITNRL
DRLAKETGCTLAGSGYQDVFWGNLISVLAGATHRIDRIEGVTSYNVEDYGIALAKVHGAG
LSKEDFRREIAENDSLPSYVWNSNEWLCSQMGWTIKGMKQELVPTFHDVPLKSETLGTTI
PAGHATGMSAVVTTETYQGPVIVTQCIGKVYAPGEVDRNDWVLKGEPNTTVQIACPATVE
LTCATLVNRLPDLLLSPAGFFTTEKMPAAAYRTYPLHLYVR

**SEQ ID NO:5 : Enzyme of Uniprot code K0UKT5 from *Mycobacterium vaccae* ATCC 25954**
MQMSGVRAVVYGVGAMNSIIAGMLIDKGVEIVGAIARSPQKVGQDLGDVIGFGRQLGVTV
SDDAAAVFAQTRPDVAVIAVNSYLTDAVEQLRICAEHGVNAVTLSEEMLYPWETSPELAA
ELDALAKSTGATLTGTGFQDTFWVNIVALLMGTAHRIDTVCGKASWNVDDFGPELATAQQ
VGRAVAEFEEWVRGAQRPPTFGRNVLDALVADTGLTVSSISTTTRPDIAFAAMRSEALGI
DLAPGDVVGFTDIDRIETAEGPAFVFEMSGRVYGTGEGDINEWTIEGEPNLFLSNGTVPT
QTTTCTQLVNRIPDVIAAPPGIVTVDKLPRLRYRTRF

**SEQ ID NO:6 : Enzyme of Uniprot code A0A101AWU7 from *Mycobacterium sp.* GA-2829**
MGPIKAVVYGVGAMNSIATRMLLDKGVEVVGAIARSEAKVGRDLGEVAGLGRELGVAVSG
DAAEVFRRTSPDVAVIAVNSYLADAVEQLRICAEHGVNAVTLSEEMLYPWNTSPGLAEEL
DAAAKRTGVTLTGTGFQDTFWVNQIALLMGTVHRIDSVSGRASWNVDDFGPELARDQQVG
CSVAEFHDWLRDAERPPTFGRNVLDALIADTGLTPTSVTSTTRPDVAAAPMFSQALQIEV
PAGSVIGITDVDEIKTEQGPSFLFEMSGRVYGVDEGDINEWEISGEPDVVLSNGTVPTQL
TTCTQLVNRIPDVIAARPGIITVDELARLRYRAFPLHTYLRGA

FIGURE 1

METHOD FOR PREPARING AMINES FROM ALDEHYDES AND KETONES BY BIOCATALYSIS

CROSS-REFERENCE TO RELATED APPLICATION

This application is the U.S. national stage application of International Patent Application No. PCT/EP2018/068288, filed Jul. 5, 2018.

The Sequence Listing for this application is labeled "Seq-List.txt" which was created on Dec. 4, 2019 and is 27 KB. The entire content of the sequence listing is incorporated herein by reference in its entirety.

FIELD OF THE INVENTION

The present invention relates to the preparation of amines from aldehydes and ketones by reductive amination with an enzymatic catalyst.

BACKGROUND OF THE INVENTION

Chiral amines are present in many active compounds and are among the most frequently used chemical intermediates for the production of agrochemicals, pharmaceutical ingredients, and polymers. For instance, an analysis of drugs approved by the FDA in recent years reveals that about 80% of new chemical entities contain one or several chiral amine moieties. Chiral secondary or tertiary amines are mostly prepared by alkylation and/or amidation of chiral primary amines. The recovery of the enantiomeric or diastereoisomeric amine of interest can be performed by kinetic crystallization resolution. Alternatively, the two most established chemical methods for preparing chiral primary amines are the asymmetric addition of carbanions to aldimines generated from aldehyde and the asymmetric hydrogenation of acetamides and imines obtained from ketones followed by cleavage of the resulting tertiary amines obtained. None of these methods enable direct access to a chiral primary amine from ketone without stepping through a secondary imine or protecting the amine intermediate.

Moreover, these methods generally request the use of expensive transition metal complexes and generate large amounts of waste via protection and deprotection steps. There is thus a real need for synthesis methods enabling to prepare primary chiral amines from prochiral ketones. The problem was partially solved by biocatalysis. Imine reductases (IRED) can catalyze the asymmetric reduction of imines and iminium ions and can, in theory, give access to a large variety of primary, secondary, or tertiary amines. However, the imine or iminium substrate should be either pre-formed or generated in situ by the condensation of amines with carbonyl compounds (Schrittwieser et al., Adv. Synth. Catal. 2015, 357, 1655-1685).

Another major contribution has come in the form of amino acid dehydrogenases, which found broad applications in the synthesis of L or D-amino acids by reductive amination of α-keto acids. In particular, L-selective amino acid dehydrogenases (L-AADH-) are ubiquitous enzymes with central roles in amino acid metabolism, which catalyze the reductive amination of α-keto acids with ammonia as well as the reverse reaction, namely the oxidative deamination of α-amino acids. Unfortunately, the substrate scope of L-AADHs is strictly limited to α-amino acids and corresponding α-keto acids. Hence, wild-type L-AADHs are not able to convert ketones lacking a vicinal carboxyl group into chiral amines (Schrittwieser et al., supra).

As of today, no gene encoding for a wild-type bacterial enzyme able to perform the reductive amination of aldehydes and ketones devoid of any close carboxylic acid moiety (e.g. at position α, β or γ position) has been identified.

Thus, the identification of amine dehydrogenases (which can be also called reductive aminases) with broad substrate scope is generally referred as "the holy grail" in biocatalysis.

Artificial amine dehydrogenases have been created via semi-rational protein engineering of existing AADH scaffolds. Bommarius et al. were the first to report the rational design of amine dehydrogenases using α-amino acid dehydrogenases, namely L-leucine dehydrogenase from *Bacillus stearothermophilus* and L-phenylalanine dehydrogenase from *Bacillus badius* as the starting scaffold (U.S. Pat. No. 8,835,136). The resulting mutants catalyze the reversible reductive amination of various ketones including hydrophobic ones through the development of a biphasic aqueous-organic solvent reaction system. The biocatalytic potential of L-phenylalanine dehydrogenase (PheDH) mutant was highlighted in a dual-enzyme hydrogen-borrowing cascade enabling the conversion of alcohols to enantiopure amines (Mutti et al., Science, 2015, 349, 1525-1529). Pushpanath et al. disclosed a newly engineered amine dehydrogenase obtained from PheDH from *Caldalkalibacillus thermarum* and able to convert several non-functionalized ketones into amines (Pushpanath et al, ACS Catal. 2017, 7, 3204-3209).

Certainly, wild-type AmDH activity was detected by Itoh at al. on isolated enzymes from *Streptomyces virginiae* but with low enantioselectivity (U.S. Pat. No. 6,432,688, Itoh, J. Mol. Catal. B: Enzym, 2000, 10, 281-290) and by Wang et al. on whole cells of *Pseudomonas kilonensis* (CN103224963) or crude enzyme solution of *Pseudomonas balearica* (CN105567756). However, in both cases, the gene sequences encoding for these amine dehydrogenase enzymes have not been identified. On the other hands, Mayol et al. recently identified a dehydrogenase from *Petrotoga mobilis* which is active towards γ-keto acids such as 2-amino-4-oxopentanoic acid and 4-oxopentanoic acid. The enzyme was shown to be inactive towards non-functionalized ketones such as acetophenone, cyclohexanone, pentan-2-one, or hexan-2-one, suggesting that the presence of a carboxylic group in the ketone is a prerequisite for the enzymatic conversion (Mayol et al., Catal. Sci. Technol., 2016, 6, 7421-7428). Very recently, Aleku et al. describe a wild-type NADP(H)-dependent reductive aminase from the filamentous fungus *Aspergillus oryzae*, capable of catalyzing the reductive coupling of carbonyl compounds with a variety of primary and secondary amines. This enzyme is also able to catalyze the reduction of a broad scope of cyclic imines and iminium ions. Aleku et al. suggest that this enzyme is a representative member of a subclass of IREDs that has evolved to possess a particular capability for catalyzing the formation of imines additionally to their reduction (Aleku et al., Nature Chemistry, 2017, DOI:10.1038/NCHEM.2782). However, the enzyme described in Aleku et al. shows a poor reactivity towards ammonia as amine donor and gives access to a very limited number of primary amines with a low percentage of conversion (see table 1 page 4 of Aleku).

As of today, the enzyme of Aleku et al. is the sole example of wild-type enzymes able to promote the reductive amination of carbonyl compounds devoid of carboxyl group and no bacterial wild-type AmDH has been identified yet.

Therefore, there is a need of new enzymes for preparing amine compounds, in particular primary amines, from aldehyde and ketones.

SUMMARY OF THE INVENTION

The invention relates to the use of an enzyme having a reductive aminase (RedAm) activity and comprising a polypeptide having at least 50% of sequence identity with an amino acid sequence preferably selected from the group consisting of SEQ ID NO:1, SEQ ID NO:2, SEQ ID NO:3, SEQ ID NO:4, SEQ ID NO:5, and SEQ ID NO:6, preferably SEQ ID NO:1-5, as a catalyst, in the reductive amination of a carbonyl-containing compound selected from aldehydes and ketones devoid of any carboxyl group at position gamma of the carbonyl group.

The invention also relates to a method for preparing an amine or a salt thereof, said method comprises the step of contacting a carbonyl-containing compound of formula (I)

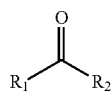
(I)

wherein $R_1$ and $R_2$ are independently selected from H, alkyl, heteroalkyl, alkenyl, aryl, heteroaryl, arylalkyl, heteroaryl alkyl, aryl alkenyl, heteroaryl alkenyl, alkyloxy alkyl, heteroaryloxy alkyl, aryloxy alkyl, and alkanoyl alkyl, said groups being optionally substituted, with proviso that $R_1$ and $R_2$ are not both H, or $R_1$ and $R_2$ form together a saturated or non-saturated ring optionally substituted and/or optionally fused with another ring, and wherein the carbonyl-containing group is devoid of any carboxyl group at position gamma of the carbonyl, with an enzyme having a reductive aminase (RedAm) activity and comprising a polypeptide having at least 50% of sequence identity with an amino acid sequence preferably selected from the group consisting of SEQ ID NO:1, SEQ ID NO:2, SEQ ID NO:3, SEQ ID NO:4, SEQ ID NO:5, and SEQ ID NO:6, preferably SEQ ID NO:1-5, in the presence of a nitrogen source, and in the presence of a cofactor selected from NADH, NADPH, synthetic analogs thereof and combinations thereof.

The resulting amine formed by the method of the invention is preferably of formula (II),

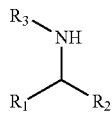
(II)

wherein $R_1$ and $R_2$ as defined in formula (I) for the carbonyl-containing compound and $R_3$ is selected from H, alkyl, alkenyl, alkynyl, and aryl, said groups being optionally substituted. The nitrogen source used in the method of the invention is typically $R_3NH_2$ or a salt thereof, wherein $R_3$ is as defined in formula (II). In some embodiments, $R_3$ is H and the source of nitrogen used in the method of the invention is ammonia or an ammonium salt.

In some embodiments, the resulting amine of formula (II) is chiral and obtained in enantiomeric excess.

In some other embodiments in the use and method of the invention, the carbonyl-containing compound has a molecular weight lower than 800 g·mol$^{-1}$, preferably lower than 600 g·mol$^{-1}$, more preferably lower than 500 g·mol$^{-1}$ and even more preferably lower than 400 g·mol$^{-1}$.

The carbonyl-containing compound may be a compound of formula (I):

wherein
  $R_1$ and $R_2$ are independently selected from the group consisting of H, $C_1$-$C_{10}$ alkyl, $C_1$-$C_{10}$ heteroalkyl $C_2$-$C_{10}$ alkenyl, $C_6$-$C_{12}$ aryl, $C_4$-$C_{12}$ heteroaryl, $C_6$-$C_{14}$ heteroaryl alkyl, $C_7$-$C_{14}$ arylalkyl, $C_8$-$C_{14}$ aryl alkenyl, $C_2$-$C_{10}$ alkyloxy alkyl, $C_7$-$C_{14}$ aryloxy alkyl, $C_5$-$C_{14}$ heteroaryloxy alkyl and $C_2$-$C_{10}$ alkanoyl alkyl, said groups being optionally substituted by one or several substituents selected from OH, NH$_2$, SH, NO$_2$, —CN, halogen, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, —COX, —C(X)$_3$ with X is a halogen, CONH$_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl, with proviso that $R_1$ and $R_2$ are not simultaneously H, or
  $R_1$ and $R_2$ form together a saturated or unsaturated 4-7-member ring optionally substituted and optionally fused to another 4-7-member ring, the one or several optional substituent(s) being selected from OH, NH$_2$, SH, NO$_2$, —CN, halogen, oxo group, $C_1$-$C_6$ alkyl, $C_1$-$C_6$ alkoxy, $C_1$-$C_6$ hydroxyalkyl, $C_1$-$C_6$ halogenoalkyl, C aminoalkyl, —COX, —C(X)$_3$ with X is a halogen, —CONH$_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl.

In some particular embodiments, of the method or use of the invention, $R_1$ and $R_2$ are independently selected from the group consisting of H, $C_1$-$C_{10}$ alkyl, $C_2$-$C_{10}$ alkenyl, $C_6$-$C_{12}$ aryl, $C_7$-$C_{14}$ arylalkyl, and $C_8$-$C_{14}$ arylalkenyl, said groups being optionally substituted by one or several substituents selected from OH, NH2, SH, NO$_2$, —CN, halogen, $C_1$-$C_4$ alkyl, $C_1$-$C_4$ alkoxy, $C_1$-$C_4$ hydroxyalkyl, $C_1$-$C_4$ halogenoalkyl, $C_1$-$C_4$ aminoalkyl, and —C(X)$_3$ with X is a halogen, with proviso that $R_1$ and $R_2$ are not simultaneously H, or $R_1$ and $R_2$ forms together a ring such that the carbonyl-containing compound is of formula (Ia):

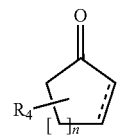

wherein n is an integer selected from 0, 1 or 2, ===== means a double or a single bound, and $R_4$ is a substituent selected from H, $C_1$-$C_4$ alkyl, an oxo group, —OH, NH$_2$, SH, NO$_2$, —CN, halogen, $C_1$-$C_4$ alkoxy, $C_1$-$C_4$ hydroxyalkyl, $C_1$-$C_4$ halogenoalkyl, $C_1$-$C_4$ aminoalkyl, and —C(X)$_3$ with X a halogen.

In some further embodiments, $R_1$ and $R_2$ are independently selected from H, phenyl, $C_1$-$C_4$, alkyl and $C_1$-$C_4$, alkenyl, said groups being optionally substituted by a substituent selected from OH and $C_1$-$C_3$ alkyl, with proviso that $R_1$ and $R_2$ are not simultaneously H, or $R_1$ and $R_2$ forms together a ring such that the carbonyl-containing compound is of formula (Ia):

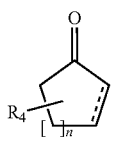

(Ia)

wherein n is 1 or 2, ===== means a double or a single bound, and $R_4$ is H or a $C_1$-$C_3$ alkyl. In some embodiments of the method or the use of the invention, the enzyme having a reductive aminase activity is a wild-type enzyme or a variant of a wild-type enzyme, said wild-type enzyme being identified from a bacteria belonging to a genus selected from *Mycobacterium, Cystobacter, Microbacterium,* and *Aminomonas*.

In some other or additional embodiments, the enzyme having a reductive aminase activity is a wild-type enzyme or a variant having at least 60% of sequence identity with an amino acid sequence selected from SEQ ID NO:1, SEQ ID NO:3, SEQ ID NO:5 and SEQ ID NO:6, preferably SEQ ID NO:1, SEQ ID NO:3 and SEQ ID NO:5.

In a particular embodiment, the enzyme having a reductive aminase activity is a wild-type enzyme or a variant having at least 50% of sequence identity with an amino acid sequence selected from SEQ ID NO:2, and SEQ ID NO:4.

In the method or use according to the invention, the enzyme having a RedAm activity may be provided as a purified or a semi-purified enzyme, an enzyme immobilized on a solid support, or is produced in situ by a wild-type cell or a host cell capable of producing said enzyme.

The method of the invention may further comprise one or several (e.g. 2, 3 or 4) of the following steps:
  a step of preparing the carbonyl compound of formula (I), for instance by oxidation of the corresponding alcohol,
  a step of recovering the amine of formula (II),
  a step of purifying the amine of formula (II)(II),
  a step of recovering the enzyme having a RedAm activity from the reaction medium.

A further object of the invention is a method for producing a compound of interest, which comprises the steps of:
  Preparing an amine of formula (II) as defined above,
  Preparing the compound of interest from the resulting amine of formula (II).

In an additional aspect, the invention relates to the use of an enzyme having a reductive aminase (RedAm) activity and comprising a polypeptide having at least 50% of sequence identity with an amino acid sequence preferably selected from the group consisting of SEQ ID NO:1, SEQ ID NO:2, SEQ ID NO:3, SEQ ID NO:4, SEQ ID NO:5 and SEQ ID NO:6, preferably SEQ ID NO:1-5, as a catalyst, in the oxidative deamination of a primary or secondary amine devoid of any carboxyl group at position gamma of the amino group.

FIGURES

FIG. 1 shows the sequence identity matrix for the enzymes according to the invention. The enzyme of SEQ ID NO:1 has 66%, 75% and 90% of sequence identity with SEQ ID NO:3, SEQ ID NO:6 and SEQ ID NO:5, respectively. The enzyme of SEQ ID NO:2 has 58% of sequence identity with SEQ ID NO:4. The sequence identities were determined using a multiple sequence alignment generated thanks to the webtool Clustal Omega developed by EBI (see Worldwide Web site: ebi.ac.uk/tools/msa/clustalo/) using default settings.

MS conditions: electrospray ionization, positive mode; theoretical mass [M+H]=192.2; [M+MeCN+H]=233.2; [2M+H]=383.2.

Figure 5:
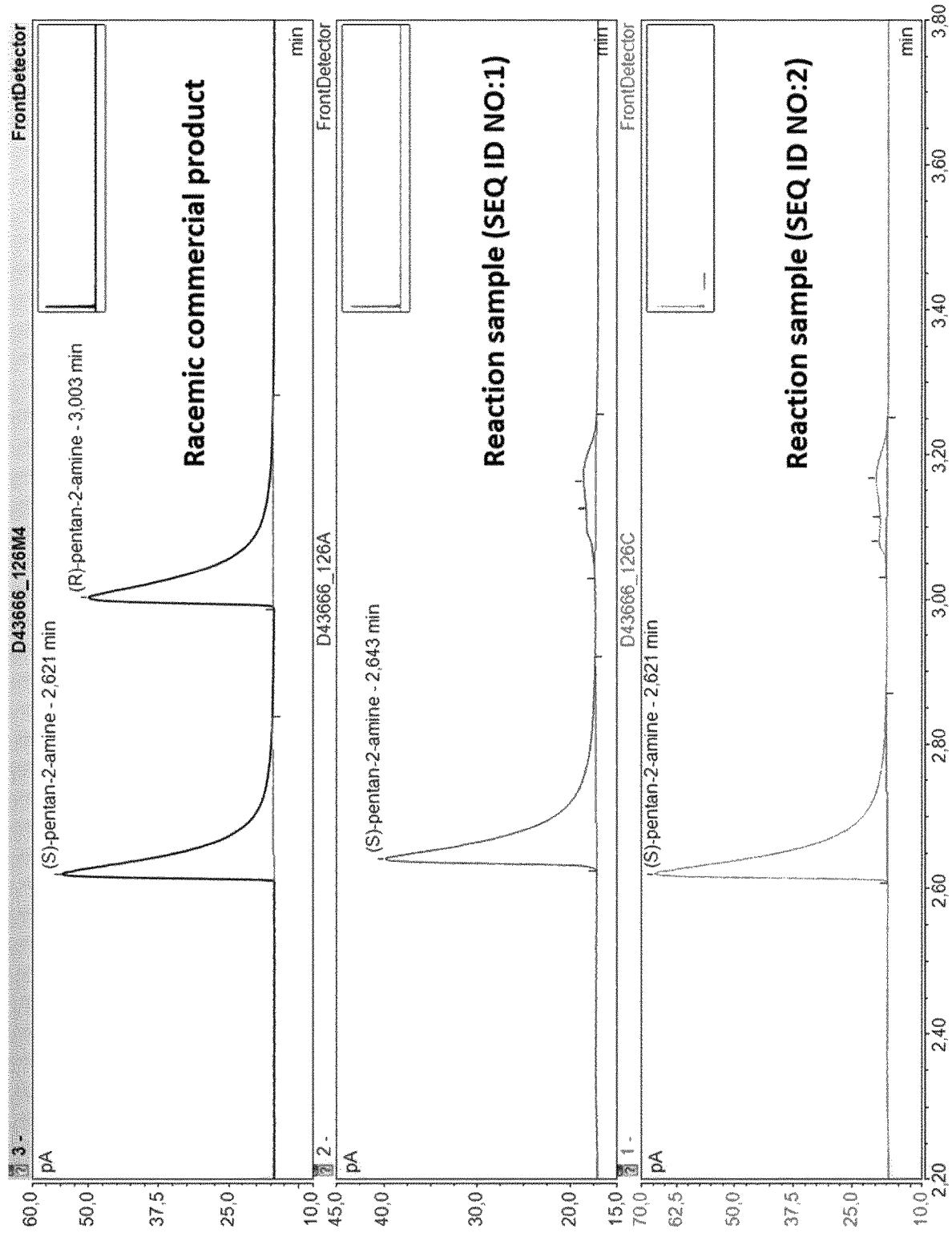

FIG. 5 shows chiral GC-FID chromatograms of racemic commercial pentan-2-amine and reaction sample corresponding to the reaction of pentan-2-one with the enzyme of SEQ ID NO:1 or SEQ ID NO:2, after derivatization with acetic anhydride/DMAP.

Figure 6:
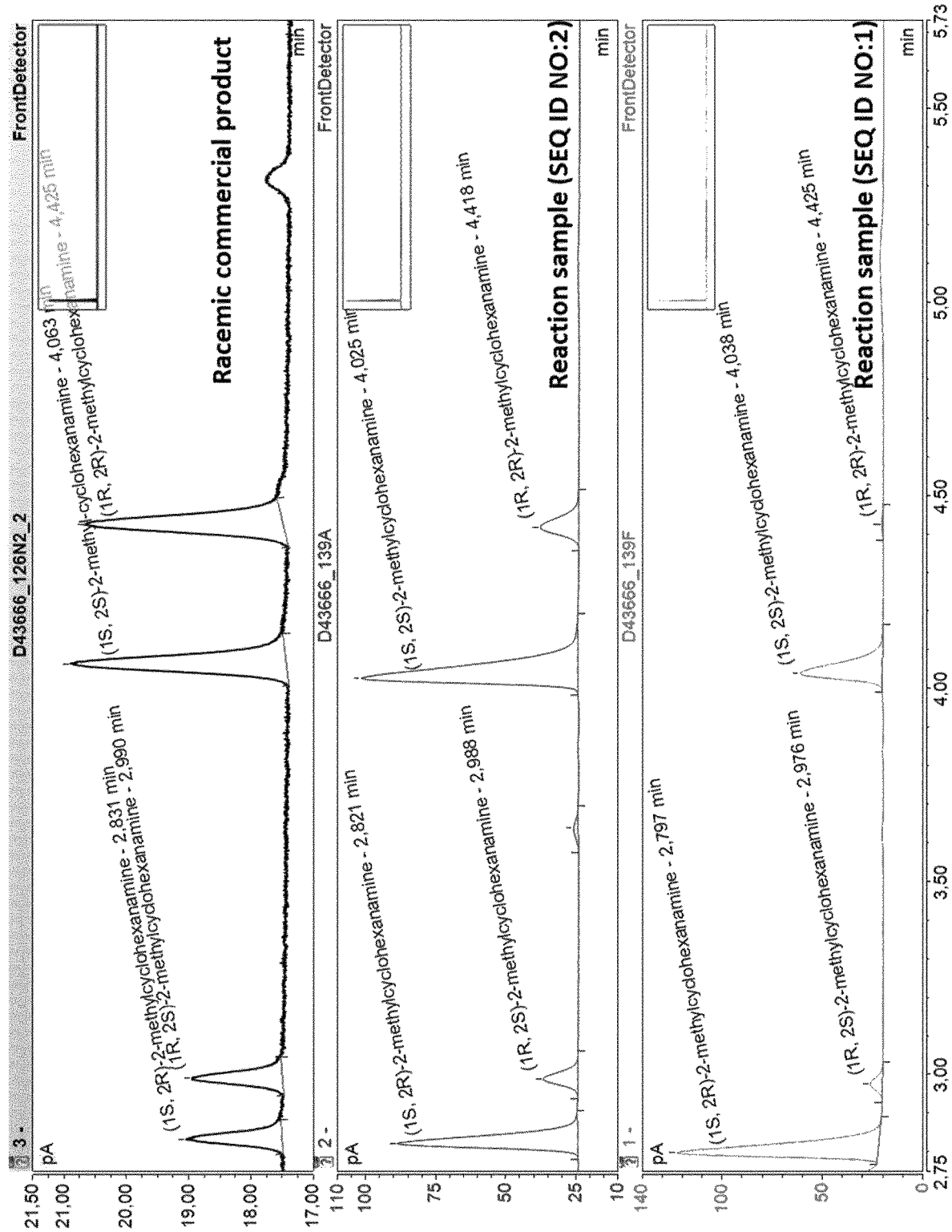

FIG. 6 shows chiral GC-FID chromatograms of racemic commercial 2-methylcyclohexanamine and reaction sample corresponding to the reaction of racemic 2-methylcyclohexanone with the enzyme of SEQ ID NO:1 or SEQ ID NO:2, after derivatization with TFAA.

Figure 7:
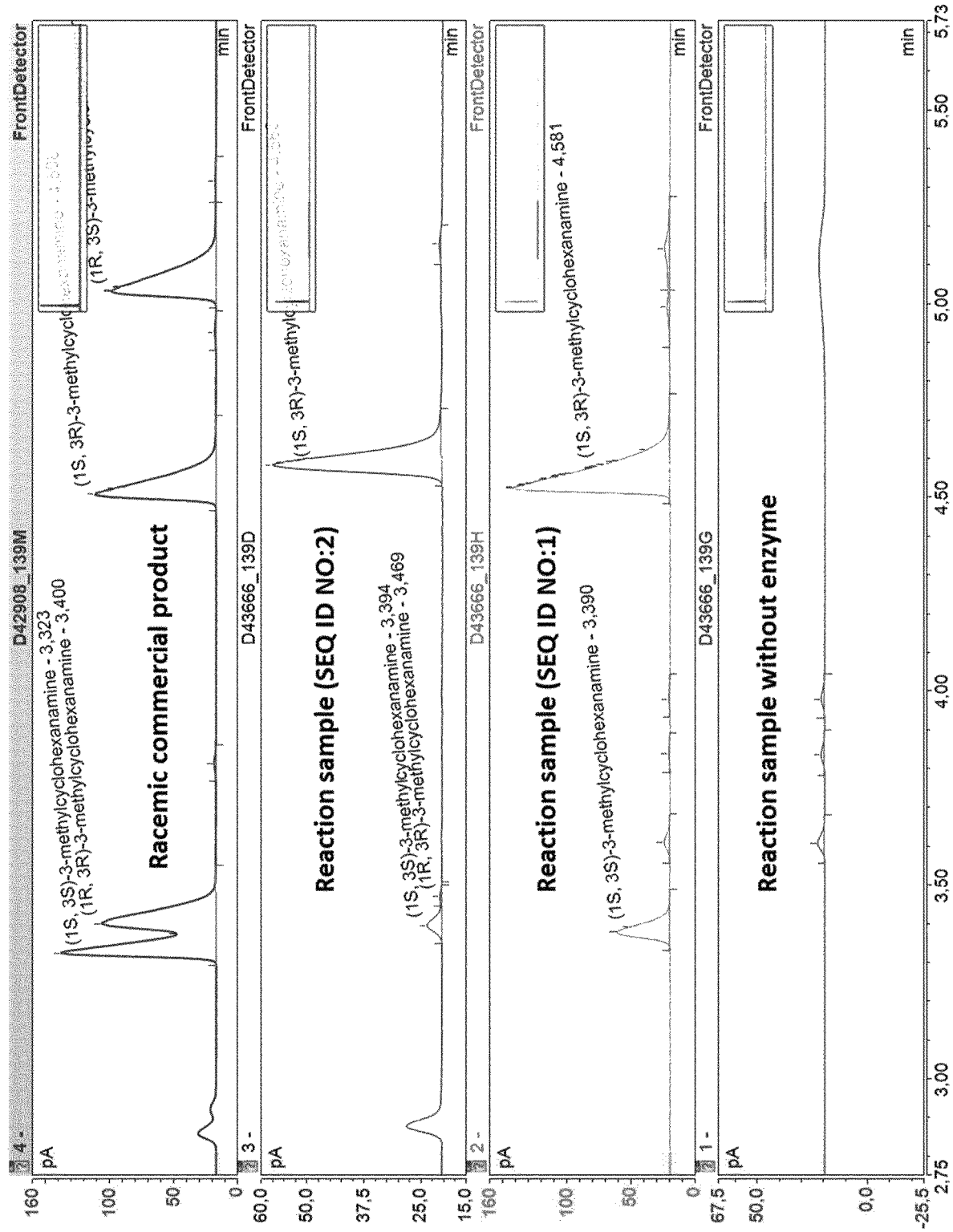

FIG. 7 shows chiral GC-FID chromatograms of racemic commercial 3-methylcyclohexanamine, reaction sample corresponding to the reaction of racemic 3-methylcyclohexanone with the enzyme of SEQ ID NO:1 or SEQ ID NO:2, after derivatization with TFAA and blank reaction without enzyme.

DETAILED DESCRIPTION OF THE INVENTION

As of today, there is no identified and characterized wild-type bacterial NAD(P)H-dependent reductive aminase able to catalyze the reductive amination of aldehydes and ketones substrates, in particular those devoid of any carboxyl group. For the first time, the Inventors identified bacterial wild-type enzymes (including their amino acid sequences) able to catalyze the reductive amination of a broad scope of aldehydes and ketones substrates in the presence of NADPH and/or NADH as cofactors and in the presence of a source of $NH_3$ in vitro. These enzymes were also shown to catalyze the reverse oxidative deamination in vitro. The Inventors identified a first subgroup of enzymes from species belonging to *Mycobacterium* and *Microbacterium* genus. The amino acid sequences of these enzymes are shown in SEQ ID NO:1, SEQ ID NO:3, SEQ ID NO:5 and SEQ ID NO:6. These enzymes have the Uniprot codes A0A0D6I8P6, C3UMY1, K0UKT5 and A0A101AWU7, respectively and are annotated as putative dihydrodipicolinate reductase N-terminus domain-containing protein in Uniprot, which correspond to enzymatic activity dramatically distinct from the reductive aminase activity (RedAm activity) shown by the Inventors. Noteworthy, these enzymes have more than 60% of sequence identity together, as shown in FIG. 1.

The Inventors also identified two other enzymes from *Cystobacter fuscus* and *Aminomonas paucivorans*. These enzymes have the amino acid sequences shown SEQ ID NO:2 and SEQ ID NO:4 respectively and have 59% sequence identity together. These enzymes have respectively the Uniprot code S9Q235 without any known putative enzymatic activity predicted and E3CZE3 annotated as putative dihydrodipicolinate reductase.

As illustrated in the examples, in particular in Example 2, these enzymes were shown to catalyze the reductive amination of a wild scope of carbonyl compounds such as optionally substituted alkyl, and cycloalkyl ketones and aldehydes, e.g. cyclohexanone and 2-methylpropanal. Contrary to wild-type amino acid dehydrogenases (AAHDs) or to the wild-type enzyme from *Petrotoga mobilis* described in Mayol et al. (see supra), the enzymes of the invention are active towards ketones and aldehydes devoid of any carboxylic group at position α, β or γ of the carbonyl group. Noteworthy, the Inventors showed that the enzymes of SEQ ID NO:1-NO:4 are inactive towards 2-amino-4-oxopentanoic acid and 4-oxopentanoic acid, which are both substrates of the wild-type enzyme from *Petrotoga mobilis* described in Mayol et al. One can further note that the enzymes of the invention have an amino acid sequence which is dramatically distinct from the enzyme of Mayol et al. (see supra) or Aleku et al. (supra) as well as the L-AAHDs and the corresponding mutants described by Bommarius et al. and Pushpanath et al (see supra): the sequence identity of the enzymes of the invention with these enzymes from the prior art is less than 30%. For sake of completeness, it should be noted that the enzymes of the invention were isolated from bacterial species dramatically distinct from that described in Itoh et al. and Wang et al. (see supra).

Noteworthy, the enzymes of the invention display an unique profile of substrates. Contrary to the enzyme described in Aleku et al., the enzymes of the invention show a high reactivity when using $NH_3$ as amine donor with respect to a large variety of aldehydes and ketones, giving access to a large panel of primary amines (see further below the Example section).

To sum-up, the enzymes of the invention form a homogeneous group of enzymes characterized by a similar enzymatic profile. Moreover, on one hand SEQ ID NO:1, SEQ ID NO:3, SEQ ID NO:5 and SEQ ID NO:6 and on the other hand SEQ ID NO:2 and SEQ ID NO:4 share common structural features as depicted by the percentage of sequence identity that they have together. The wild-type RedAms of SEQ ID NO:1 and SEQ ID NO:2 identified by the Inventors are enantioselective, which means that one amine enantiomer is preferably formed when the starting substrate is a pro-chiral ketone. For instance, as shown in Example 5, when the starting ketone is pentan-2-one, (S)-pentan-2-amine is obtained with a significant enantiomeric excess. In contrast, the mutants of wild-type AAHD described by Bommarius et al. and Pushpanath et al. convert ketone substrates into (R)-amino compound (see for instance scheme 1 page 3205 of Pushpanath et al.). Moreover, as shown in Example 5 for 2-methylcyclohexanone and 3-methylcyclohexanone, the enzymes of the invention can produced the corresponding amines with high stereoselectivity at the (1S) position and selectivity for one diastereoisomer over the other.

One can further note that the enzymes of SEQ ID NO:1 and SEQ ID NO:2 have a higher specific activity for substrates such as cyclic aliphatic ketones than engineered AmDH described in Pushpanath et al. (see Example 2). High specific activities were also shown for enzyme of SEQ ID NO:3 towards substrates such as cyclohexanone, methylhexanone isomers, methyl propanal, and 3-methylbutanone (Example 2, Table 3).

In brief, the wild-type RedAm of the Invention showed an original RedAm activity profile, in particular as compared to AADH mutants described in the prior art.

Definitions

Reductive aminase or Amine Dehydrogenase: In the context of the invention, a reductive aminase (RedAm), which can be also called amine dehydrogenase (AmDH), refers to an oxidoreductase able to catalyze the reductive amination of a ketone or an aldehyde, preferably devoid of any carboxyl group at position gamma of the carbonyl, with $NH_3$, in the presence of NADH and/or NADPH as cofactor in vitro. The enzyme may also be capable of catalyzing the reverse oxidative deamination in vitro.

As used herein, a RedAm refers to enzyme able to catalyze the reductive amination of at least one carbonyl-containing compound selected from 2-methylpropanal, cyclohexanone, pentan-2-one and 2-methylcyclohexanone, preferably the reductive amination of 2-methyl-propanal and/or cyclohexanone in vitro.

In the context of the invention, an RedAm is preferably an enzyme able to convert 2-methylpropanal into isobutylamine in the presence of a source of $NH_3$ and in the presence of NADPH and/or NADH as cofactor:

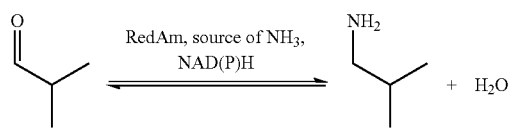

In other or additional embodiments, the reductive aminase (RedAm) can catalyze the reductive amination of cyclohexanone into cyclohexanamine in vitro:

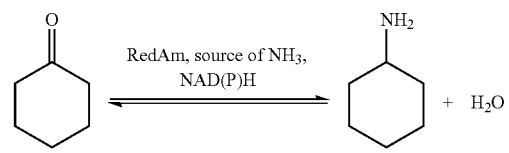

In a particular embodiment, the RedAm is capable of catalyzing:
 The reductive amination of 2-methylpropanal into isobutylamine, and
 The reductive amination of cyclohexanone into cyclohexanamine,
in the presence of NADPH and/or NADH and in the presence of a source of $NH_3$, in vitro. A source of $NH_3$ is typically an ammonium salt.

In other or additional embodiments, the RedAm can further catalyze at least one of the following reactions, in the presence of NADPH and/or NADH and in the presence of a source of NH₃, in vitro:

The reductive amination of pentan-2-one into pentan-2-amine, and

The reductive amination of 2-methylcyclohexanone into 2-methylcyclohexanamine.

Preferably, said amine(s) is/are obtained in enantiomeric excess, e.g. in an enantiomeric excess of more than 80%, 90%, 95% or 98%. For instance, the enzymes of SEQ ID NO:1 and SEQ ID NO:2 lead to a pentan-2-amine enantiomer and a 2-methylcyclohexanamine diastereoisomer wherein the configuration of the carbon bearing the amino group is predominantly (S).

Assessment of reductive aminase activity: In the context of the invention, "reductive aminase (RedAm) activity" refers to the ability of a given enzyme to catalyze the reductive amination of an aldehyde or a ketone such as 2-methylpropanal, cyclohexanone, 2-methylcyclohexanone and pentan-2-one in vitro. As mentioned above, a model substrate is 2-methylpropanal which is converted into isobutylamine. The reaction preferably takes place in the presence of NADH and/or NADPH as cofactor and in the presence of a source of NH₃. The source of NH₃ is typically ammonia and/or an ammonium salt.

The ability of an enzyme to display RedAm activity can be assessed in vitro by contacting the enzyme with the carbonyl-containing substrate and the source of NH₃, in the presence of NADPH and/or NADH in conditions conducive for the enzyme activity. The enzymatic activity can be detected, for instance, by detecting the formation of the amine product (e.g. by HPLC UV-MS, optionally after derivatization with benzoyl chloride or dinitrofluorobenzene or by GC-FID optionally after derivatization with acetic anhydride or trifluoroacetic anhydride or indirectly by measuring the decrease in absorbance at 340 nm by spectrophotometry, which indicates the depletion of NAD(P)H cofactor in the reaction medium.

For instance, the assessment of the RedAm activity can be implemented in the following conditions:

Buffer: 2 M ammonia/ammonium formate (NH₃/HCOONH₄ at pH 9.5)

Cofactor: 0.2 mM NAD(P)H

Ketone substrate: 10 mM

Enzyme concentration: variable, typically from 0.025 to 0.5 mg·ml⁻¹

Carboxyl group: a carboxyl group refers to —COOH or a salt thereof.

Carbonyl-containing compound: a carbonyl-containing compound (also called carbonyl compound) refers to a compound containing the following moiety

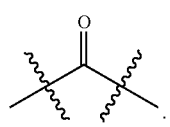 [SMILES: *C(*)=O]

Carbonyl-containing compounds encompass ketones and aldehydes.

Ketone: as used herein, a ketone refers to a carbonyl-containing compound having the following formula:

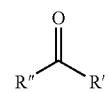

in which R' and R" are not H. A "prochiral ketone" refers to a ketone for which the amine resulting from its reductive amination is chiral, because the carbon bearing the amine group is asymmetric. An example of prochiral ketone is for instance a ketone wherein R' and R" are different or wherein R' and R" form together a 6-member ring comprising one substituent at position alpha or beta of the carbonyl group.

Aldehyde: as used herein, an aldehyde refers to a carbonyl-containing compound having the following formula:

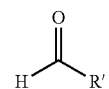

wherein R' is not H.

In some embodiments, the ketone or the aldehyde do not have any carboxyl moiety at position γ of the carbonyl group. In some other or additional embodiments, the ketone or the aldehyde may not have any carboxyl group at position α or β of the carbonyl group. It goes without saying that said ketone or said aldehyde can bear other substituents such as alkyl substituents and hydroxyl at positions α, β or γ of the carbonyl group.

The positions α, β or γ of the carbonyl group are shown in the below Figure:

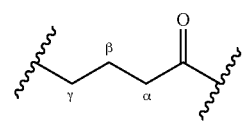 [SMILES: *CCCC(*)=O]

Alkyl: as used herein, an alkyl refers to any straight or branched chain or cyclic chain hydrocarbon radical wherein carbon-carbon bonds are simple bonds. A $C_1$-$C_6$ alkyl encompasses, without being limited to, methyl, ethyl, propyl, isopropyl, cyclopropyl, butyl, isobutyl, tert-butyl, cyclobutyl, pentyl, cyclopentyl, hexyl, and cyclohexyl. The alkyl group may be substituted or unsubstituted.

Saturated compound: As used herein, a saturated compounds refers to a compound wherein the C—C bonds are single, namely a compound devoid of any C=C or C≡C bond. An unsaturated compound refers to a compound which contains at least one C=C or C≡C bond.

Alkenyl: refers to a radical of formula $Alk_1$-C=C-$Alk_2$ wherein $Alk_1$ and $Alk_2$ are alkyl.

Heteroalkyl: as used herein, a heteroalkyl refers to an alkyl wherein the backbone comprises one or several (e.g. 2, 3, or 4) heteroatoms preferably selected from O, N and S. Typically, the heteroalkyl comprises at least one moiety:

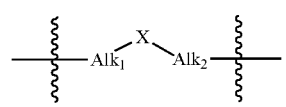

wherein X is O, NH or S and $Alk_1$ and $Alk_2$ are alkyl radicals. The heteroalkyl can be cyclic or acyclic.

Haloalkyl or halogenoalkyl: a haloalkyl refers to an alkyl bearing at least one (e.g. 1, 2, 3 or 4) halogen as substituent. The halogen may be F, Cl, Br and I, preferably F or Cl.

Alkoxy: an "alkoxy" refers to a radical of formula Alk-O— wherein Alk represents an alkyl group.

Aryl: an aryl refers to an aromatic ring system which has 5-14 ring atoms and at least one ring having a conjugated pi electron system. An aryl may contain more than one aromatic ring such as fused ring systems or an aryl group substituted with another aryl group. Aryl encompass, without being limited to, phenyl, anthracyl, naphtyl, and biphenyl. An aryl may be substituted or unsubstituted. A preferred aryl group is phenyl optionally substituted.

Aryloxy: an "aryloxy" refers to a radical of formula Ar—O— wherein Ar represents an aryl group.

Aryloxyalkyl: an aryloxyalkyl refers to a radical of formula Ar—O—Alk- wherein Ar represents an aryl group and Alk represents an alkyl group.

Alkyloxyalkyl group: an "alkyloxyalkyl" refers to a radical of formula Alk1-O-Alk2- wherein each Alk1 and Alk2 are independently selected from alkyls. Alkyloxyalkyl is an example of heteroalkyl radicals.

Alkanoyl alkyl: an "alkyloxyalkyl" refers to a radical of formula Alk1-(C=O)-Alk2- wherein each Alk1 and Alk2 are independently selected from alkyls.

Heteroaryl: as used herein, "heteroaryl group" refers to a chemical group having 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Heteroaryl groups include, without being limited to, furanyl, thienyl, pyridyl, pyrrolyl, N-alkyl pyrrolyl, pyridyl-N-oxide, pyrimidyl, pyrazinyl, imidazolyl, benzimidazolyl, benzofuranyl, benzothiophenyl, quinazolinyl, quinolinyl, and the like. The heteroaryl group may be substituted or unsubstituted. A preferred heteroaryl group is pyridyl optionally substituted.

Heteroaryloxy alkyl: a "heteroaryloxy alkyl" refers to a radical of formula Het-O-Alk- wherein Het represents a heteroaryl group and Alk represents an alkyl.

Aryl alkyl: as used herein, an "aryl alkyl" refers to a radical of formula Ar-Alk- wherein Ar is an aryl group and Alk is an alkyl. An example of aryl alkyl is Ph-$(CH_2)_p$— wherein Ph is a substituted or unsubstituted phenyl and p is an integer from 1 to 6.

Heteroaryl alkyl: as used herein, a "heteroaryl alkyl" refers to a radical of formula HetAr-Alk- wherein HetAr is a heteroaryl group and Alk is an alkyl.

Substituted: as used herein, a substituted group refers to groups substituted by one or several substituents, typically 1, 2, 3, 4, 5 or 6 substituents. For instance, the substituents may be independently selected from $C_1$-$C_6$ alkyl, aryl group, $C_3$-$C_6$ cycloalkyl, $C_2$-$C_6$ heterocycloalkyl, $C_1$-$C_6$ alkoxy, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, —$N_3$, —$NH_2$, —F, —I, —Br, —OH, —Cl, —SH, $C_1$-$C_6$ alkanoyl, $C_1$-$C_6$ acylamino, —$CONH_2$, —$NO_2$, OP(=O)(OH)$_2$, —$SO_3$H, $C_1$-$C_6$ hydroxyalkyl, $C_1$-$C_6$ haloalkyl, $C_1$-$C_6$ alkylthio, $C_2$-$C_{10}$ alkoxy alkyl, $C_2$-$C_6$ alkoxy carbonyloxy, —CN, —$CF_3$, —COOH, —C(=O)—R, —NHC(=O)R, —C(=O)NHR, SC(=O)R, —C(=O)SR, —OC(=O)R, and —C(=O)OR, wherein R is a $C_1$-$C_6$ alkyl. In particular, the substituent(s) may be selected among halogens, in particular F or Cl, —OH, $C_1$-$C_6$ alkoxy, $C_1$-$C_6$ alkyl, $C_1$-$C_6$ hydroxyalkyl, and $C_1$-$C_6$ halogenoalkyl. When present, a COOH substituent is preferably at a position other than at a position γ of the carbonyl group, and even at a position other than at position α, β, and γ of the carbonyl group.

The wording "optionally substituted" can be replaced by the wording "substituted or unsubstituted" throughout this application.

Oxo group or substituent: An oxo substituent refers to the presence of a substituent of formula

For instance, as used herein, a cyclohexane substituted with an oxo group refers to cyclohexanone:

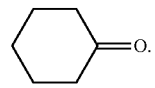

Expression: the term "expression" includes any step involved in the production of a polypeptide including, but not limited to, transcription, post-transcriptional modification, translation, post-translational modification, and secretion.

Isolated: the term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance).

Recombinant: recombinant refers to a nucleic acid construct, a vector and a protein produced by genetic engineering or to a cell which has been genetically modified with the nucleic construct or the vector, e.g. so as to express a heterologous gene.

Heterologous: in the context of a host cell, a vector or a nucleic acid construct, it designates a coding sequence for the enzyme introduced into the host cell, the vector or the nucleic acid construct by genetic engineering. In the context of a host cell, it can mean that the coding sequence for the enzyme originates from a source different from the cell in which it is introduced. Alternatively, it can also mean that the coding sequence for the enzyme comes from the same species as the cell in which it is introduced but it is considered heterologous due to its environment which is not natural, for example because it is under the control of a promoter which is not its natural promoter, or is introduced at a location which differs from its natural location.

Nucleic acid construct: the term "nucleic acid construct" means a nucleic acid molecule, either single- or double-stranded, which is modified to contain segments of nucleic acids in a manner that would not otherwise exist in nature or which is synthetic, which comprises one or more control sequences.

Operably linked: the term "operably linked" means a configuration in which a control sequence is placed at an appropriate position relative to a coding sequence, in such a way that the control sequence directs expression of the coding sequence.

Amino acid modifications or changes: as used herein, by "amino acid modification" is meant a change in the amino acid sequence of a polypeptide. "Amino acid modifications" which may be also termed "amino acid changes", herein include amino acid mutations such as substitution, insertion, and/or deletion in a polypeptide sequence. By "amino acid substitution" or "substitution" herein is meant the replacement of an amino acid at a particular position in a parent polypeptide sequence with another amino acid. By "amino acid insertion" or "insertion" is meant the addition of an amino acid at a particular position in a parent polypeptide sequence. By "amino acid deletion" or "deletion" is meant the removal of an amino acid at a particular position in a parent polypeptide sequence.

Parent enzyme or polypeptide: as used herein, it is meant an unmodified enzyme that is subsequently modified to generate a variant.

Variant: as used herein, a variant refers to a polypeptide sequence that differs from that of a parent polypeptide sequence by virtue of at least one amino acid modification. Typically, a variant comprises from 1 to 50 amino acid modifications, preferably from 1 to 40 amino acid modifications. In particular, the variant may have from 1 to 20 amino acid changes, e.g. 1, 2, 3, 4, 5, 6, 7, 8, 9, 10, 11, 12, 13, 14, 15, 16, 17, 18, 19, or 20 amino acid modifications as compared to its parent. The sequence of a variant may comprise one or several amino acid substitutions, and/or, one or several amino acid insertions, and/or one or several amino acid deletions as compared to the sequence of its parent. In some embodiments, the amino acid modifications are conservative, preferably conservative substitutions. In other words, the amino acid modifications present in the variant do not significantly change its properties as compared to its parent. Conservative substitutions and the corresponding rules are well-described in the state of the art. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill (1979, In, The Proteins, Academic Press, New York). Common substitutions are the followings Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly. Alternatively, the amino acid modifications are of such a nature that the physico-chemical properties of the polypeptides are altered. For example, amino acid modifications may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, Science 244: 1081-1085). The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for instance, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide. Single or multiple amino acid substitutions, deletions, and/or insertions can be made and tested using known methods of mutagenesis, recombination, and/or shuffling, followed by a relevant screening procedure. Other methods that can be used include error-prone PCR, phage display, and region-directed mutagenesis.

Sequence identity: the sequence identity between two amino acid sequences is described by the parameter "percentage of identity". For purposes of the present invention, the "percentage of identity" between two amino acid sequences (A) and (B) is determined by comparing the two sequences aligned in an optimal manner, through a window of comparison. Said alignment of sequences can be carried out by well-known methods, for instance, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity may be obtained by dividing the full number of identical amino acid residues aligned by the full number of residues contained in the longest sequence between the sequence (A) and (B). Sequence identity is typically determined using sequence analysis software. For comparing two amino acid sequences, one may use, for example, the tool "Emboss needle" for pairwise sequence alignment of proteins providing by EMBL-EBI and available on see World-wide Web site: ebi.ac.uk/Tools/services/web/toolform.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Method for Preparing an Amine Compound According to the Invention

In a first aspect, the invention relates to a method for preparing an amine compound from a carbonyl-containing compound selected from ketones and aldehydes, by reductive amination. In the method of the invention, the reductive amination of the carbonyl-containing compound is catalyzed by an enzyme having a reductive aminase (RedAm) activity and preferably comprising a polypeptide having at least 50% of sequence identity with an amino acid sequence selected from SEQ ID NO:1, SEQ ID NO:2, SEQ ID NO:3, SEQ ID NO:4 and SEQ ID NO:5. The carbonyl-containing compound may be any compound of formula (II):

(I)

wherein $R_1$ and $R_2$ may be of any type.

For instance, $R_1$ and $R_2$ may be selected from H and unsubstituted or substituted, alkyl, heteroalkyl, alkenyl, aryl, heteroaryl, arylalkyl, heteroaryl alkyl, aryl alkenyl, heteroaryl alkenyl, alkyloxy alkyl, heteroaryloxy alkyl, aryloxy alkyl, and alkanoyl alkyl with proviso that $R_1$ and $R_2$ are not both H. Alternatively, $R_1$ and $R_2$ may form together a saturated or non-saturated ring optionally substituted and/or optionally fused with another ring. Typically the carbonyl-containing compound of formula has a molecular weight of less than 800 g·mol$^{-1}$, such as less than 700, 600, 550, 500, 450, 425, 400, 350, 325, 300, 275, 250, 225 or 200 g·mol$^{-1}$. In a particular embodiment, the carbonyl-containing compound is a ketone or an aldehyde devoid of any carboxyl group at position gamma of the carbonyl group.

In some other embodiments, the carbonyl-containing compound is a ketone or an aldehyde which may be devoid of any carboxyl group at position alpha, beta or gamma of the carbonyl group.

The method of the invention comprises contacting the carbonyl-containing compound with an enzyme in the presence of a source of nitrogen, for example a primary amine or a source of ammonia, in conditions conducive for the enzymatic activity. A cofactor such as NADPH and/or NADH or a synthetic analog thereof may be added in the reaction medium.

In a more particular aspect, the invention relates to the use of an enzyme having a reductive aminase activity and preferably comprising a polypeptide having at least 50% of sequence identity with an amino acid sequence selected from SEQ ID NO:1, SEQ ID NO:2, SEQ ID NO:3, SEQ ID NO:4 and SEQ ID NO:5 for preparing an amine compound or a salt thereof from a carbonyl-containing compound selected from aldehydes and ketones preferably devoid of any carboxyl group at position gamma of the carbonyl group. The enzyme of the invention is used as a catalyst, namely to catalyze the reductive amination of the carbonyl-containing compound. The invention also relates to a method for preparing an amine compound or a salt thereof comprising the step of contacting a carbonyl-containing compound of formula (I)

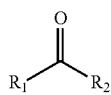

(I)

wherein

R$_1$ and R$_2$ are independently selected from H and unsubstituted or substituted alkyl, heteroalkyl, alkenyl, aryl, heteroaryl, arylalkyl, heteroaryl alkyl, aryl alkenyl, heteroaryl alkenyl, alkyloxy alkyl, heteroaryloxy alkyl, aryloxy alkyl, and alkanoyl alkyl with proviso that R$_1$ and R$_2$ are not both H, or R$_1$ and R$_2$ form together a saturated or non-saturated ring optionally substituted and/or optionally fused to another ring, with an enzyme having a reductive aminase (RedAm) activity and preferably comprising a polypeptide having at least 50% of sequence identity with an amino acid sequence selected from SEQ ID NO:1, SEQ ID NO:2, SEQ ID NO:3, SEQ ID NO:4 and SEQ ID NO:5 in the presence of a nitrogen source, and a cofactor selected from NADH, NADPH, a synthetic analog thereof and combinations thereof.

The carbonyl-containing compound of formula (I) is preferably devoid of any carboxyl group at position γ of the carbonyl group.

The resulting amine is of formula (II)

(II)

R$_1$ and R$_2$ in formula (II) of the resulting amine are as defined in formula (I) for the carbonyl-containing compound. R$_3$ depends on the nitrogen source used in the reaction.

Typically, R$_3$ is selected from H, alkyl, alkenyl, alkynyl, and aryl, said groups being optionally substituted. In some embodiments, R$_3$ is selected from H, C$_1$-C$_{10}$ alkyl, C$_2$-C$_{10}$ alkenyl, C$_2$-C$_{10}$ alkynyl and C$_6$-C$_{14}$ aryl, optionally substituted by one or several substituents selected from OH, C$_1$-C$_3$ alkyl, C$_1$-C$_3$ alkoxy, NH$_2$ and halogens.

In a preferred embodiment, R$_3$ is CH$_3$ or H, more preferably H.

The Enzyme to Implement the Method of the Invention

The method or the use of the invention is implemented with an enzyme having a reductive aminase activity and comprising a polypeptide having at least 50% of sequence identity with an amino acid sequence selected from the group consisting of SEQ ID NO:1, SEQ ID NO:2, SEQ ID NO:3, SEQ ID NO:4, SEQ ID NO:5 and SEQ ID NO:6, preferably SEQ ID NO:1, SEQ ID NO:2, SEQ ID NO:3, SEQ ID NO:4 and SEQ ID NO:5.

As mentioned in the definition section, a reductive aminase activity refers to the ability of a given enzyme to catalyze in vitro the reductive amination of at least one carbonyl-containing compound selected from 2-methylpropanal, cyclohexanone, pentan-2-one and 2-methylcyclohexanone.

In a particular embodiment, the reductive aminase (RedAm) of the invention catalyzes the reductive amination of 2-methylpropanal into isobutylamine in vitro.

In certain embodiments, the reductive aminase (RedAm) of the invention can further catalyze the reductive amination of cyclohexanone into cyclohexanamine in vitro. In another or additional embodiment, the reductive aminase (RedAm) of the invention can further catalyze the reductive amination of pentan-2-one into pentan-2-amine, and/or the reductive amination of 2-methylcyclohexanone into 2-methylcyclohexanamine in vitro.

This activity can be detected as described in the "definition" section or below in the "Examples" section.

The enzyme implemented in the invention preferably needs NADPH and/or NADH as cofactor in order to catalyze such reductive amination. In other words, the enzyme of the invention may be NAD(P)H-dependent. In certain embodiments, a synthetic analog of NADPH or NADH can be used.

As used herein, "At least 50% of sequence identity" encompasses a percentage of sequence identity of at least 55%, 60% 65%, 70%, 75%, 80%, 85%, 90%, 93% 95%, 96%, 97%, 98% and 99%.

In some embodiments, the enzyme having a reductive aminase activity comprises a polypeptide having at least 60%, 70%, 75%, 80%, 85% or 90% of sequence identity with an amino acid sequence selected from the group consisting of SEQ ID NO:1, SEQ ID NO:2, SEQ ID NO:3, SEQ ID NO:4, SEQ ID NO:5 and SEQ ID NO:6, preferably SEQ ID NO:1, SEQ ID NO:2, SEQ ID NO:3, SEQ ID NO:4 and SEQ ID NO:5.

In some particular embodiments, the enzyme of the invention has an amino acid sequence having at least 50%, e.g. at least 60%, 65%, 70%, 75%, 80%, 85% 90%, or 95% of sequence identity with an enzyme from the first subgroup which comprises SEQ ID NO:1, SEQ ID NO:3, SEQ ID NO:5 and SEQ ID NO:6.

In another aspect, the enzyme used in the method of the invention may be an enzyme having a reductive aminase activity and comprising a polypeptide having at least 50%, e.g. at least 60%, 65%, 70%, 75%, 80%, 85% 90%, or 95% of sequence identity with an amino acid sequence shown in SEQ ID NO:2 or SEQ ID NO:4.

In some embodiments, the enzyme of the invention comprises, or consists in, a polypeptide of SEQ ID NO:1, SEQ ID NO:2, SEQ ID NO:3, SEQ ID NO:4, SEQ ID NO:5 or SEQ ID NO:6. The enzyme of the invention may be a wild-type isolated enzyme, namely an isolated naturally-occurring enzyme, a variant of a wild-type enzyme, or a hybrid polypeptide.

In some embodiments, the enzyme of the invention is a wild-type enzyme isolated from a microorganism, especially from a bacterium.

Based on the teaching of the present disclosure, the one skilled in the art can identify other enzymes from microorganisms having the reductive aminase (RedAm) activity as described herein. The polypeptide may be identified and obtained from microorganisms isolated from nature (e.g., soil, composts, water, etc.). Techniques for isolating microorganisms directly from natural habitats are well known in the art. Alternatively, a polynucleotide encoding an enzyme of the invention may be obtained by screening a genomic DNA, cDNA library from microorganisms, a mixed DNA sample or DNA samples obtained directly from natural materials (e.g., soil, composts, water, etc.). Once a polynucleotide encoding an enzyme of the invention, namely having the RedAm activity as defined herein, has been detected, the polynucleotide can be isolated or cloned by utilizing techniques that are known to those of ordinary skill in the art.

For instance, the enzyme of the invention may be a wild-type enzyme from a bacterial microorganism which belongs to a genus selected from *Mycobacterium, Cystobacter, Microbacterium, Williamsia,* and *Aminomonas*. Appropriate bacterial species of interest encompass, without being limited to, *Mycobacterium vaccae, Mycobacterium smegmatis, Cystobacter fuscus, Mycobacterium* sp. GA-2829, *Microbacterium* sp. MA1, *Williamsia* sp. EG1, and *Aminomonas paucivorans*. Alternatively, the enzyme of the invention may be a wild-type enzyme from a eukaryote cell, such as a filamentous fungus, e.g. belonging to *Aspergillus* genus or a yeast.

In some other embodiments, the enzyme of the invention is a variant of a wild-type enzyme. Said wild-type enzyme comprises an amino acid sequence preferably selected from the group consisting of SEQ ID NO:1, SEQ ID NO:2, SEQ ID NO:3, SEQ ID NO:4, SEQ ID NO:5 and SEQ ID NO:6 more preferably SEQ ID NO:1, SEQ ID NO:2, SEQ ID NO:3, SEQ ID NO:4 and SEQ ID NO:5. For instance, the enzyme may be variant having an amino acid sequence which differs from an amino acid sequence selected from SEQ ID NO:1, SEQ ID NO:2, SEQ ID NO:3, SEQ ID NO:4, SEQ ID NO:5 an SEQ ID NO:6 in virtue of 1 to 100 amino acid modifications, for instance from 1 to 50 or from 1 to 40 amino acid modifications, preferably from 1 to 20 amino acid modifications, namely by 1, 2, 3, 4, 5, 6, 7, 8, 9, 10, 11, 12, 13, 14, 15, 16, 17, 18, 19 or 20 amino acid modifications. As mentioned above in the "definition section", amino acid modifications encompass insertion, deletion and substitution. In some embodiments, the amino acid modifications are conservative whereby the properties of the mutant are similar to those of its parent. In some other embodiments, the variant displays modified properties as compared to its parent enzyme, for example a modified solubility in aqueous medium and/or in solvent medium, an improved stability to pH, temperature and/or organic solvent, an improved RedAm activity, and/or a modified regioselectivity or stereoselectivity as compared to the parent enzyme. The methods for obtaining variants of a given enzyme are well-known in the art. Some of them are cited herein in the "Definition" section.

In some embodiments, the enzyme of the invention is a wild-type enzyme, or a variant thereof, wherein the wild-type enzyme is from a *Mycobacterium* species or a *Microbacterium* species, and has at least 50% of sequence identity, preferably at least 60%, 70% or 80% of sequence identity, with an amino acid sequence selected from SEQ ID NO:1, SEQ ID NO:3, SEQ ID NO:5 and SEQ ID NO:6. In some other embodiments, the enzyme of the invention is a wild-type enzyme, or a variant of a wild-type enzyme, wherein the wild-type enzyme is from *Aminomas* species or a *Cystobacter* species and has at least 50% of sequence identity, preferably at least 60%, 70% or 80% of sequence identity with SEQ ID NO:2 or SEQ ID NO:4. In some further embodiments, the enzyme of the invention is a hybrid polypeptide which means that said enzyme comprises a first polypeptide having the RedAm activity of interest and having at least 50% of sequence identity with an amino acid sequence selected from SEQ ID NO:1, SEQ ID NO:2, SEQ ID NO:3, SEQ ID NO:4, SEQ ID NO:5 and SEQ ID NO:6 which is fused or conjugated to another chemical or biochemical entity. The chemical or biochemical entity can be fused or conjugated to the N- or C-terminus region of the first polypeptide.

In some embodiments, the hybrid enzyme comprises a first polypeptide having the enzymatic activity of interest which is fused to an additional polypeptide. Said additional polypeptide can be selected in order to enhance the stability of the enzyme, to promote the secretion (such as a N-terminal hydrophobic signal peptide) of the hybrid enzyme from a cell (such as a bacterial cell or a yeast cell), or to assist in the purification of the hybrid enzyme. More particularly, the additional region can be a tag useful for purification or immobilization of the hybrid enzyme. Such a tag is well-known by the person skilled in the art, for instance a His tag (His6), a FLAG tag, a HA tag (epitope derived from the Human influenza protein haemagglutinin), a maltose-binding protein (MPB), a MYC tag (epitope derived from the human proto-oncoprotein MYC), streptavidin or avidin, or a GST tag (small glutathione-S-transferase).

A conjugated polypeptide refers to a polypeptide wherein the amino acid sequence has been conjugated by chemical means to at least one chemical or biochemical entity. Techniques for conjugating an amino acid sequence to another chemical or biochemical entity are well-known in the art. The additional entity and the polypeptide having the enzymatic activity of interest may be covalently linked to each other directly or via a spacer. The spacer can be any standard linker commonly used for the preparation of polypeptide constructs. In some embodiments, the linker is a polypeptides comprising from 1 to 50 amino acid residues. Some preferred examples are Gly-Ser linkers such as tetraglycyl-seryl-triglycyl-serine peptide or polyalanine linkers. The additional chemical or biochemical entities may be of any type. For instance, the additional or biochemical entities may be a mean useful for immobilizing the enzyme, e.g. a biotin or a reactive functional group, a mean for detecting the enzyme, a label and the like.

The enzyme of the invention can be added in the reaction medium in a purified form or in a pre-purified form, for instance in the form of cell-free extract or in the form of a clarified supernatant.

The enzyme may be present in a free state or immobilized on an appropriate support. After being isolated and purified, the enzyme of interest can be immobilized on a support by any appropriate method described in the state in the art, for instance, by covalent binding, adsorption, entrapment or membrane confinement. A wide variety of supports may be used for immobilizing the enzyme. Convenient supports encompass, without being limited to, plastic, metal, inorganic support such as glass, silica, alumina, bentonite, hydroxyapatite, nickel/nickel oxide, titanium, zirconia, polymeric supports and the like. The support may be in the form of a surface, a powder, micro- or nanobeads, a gel, a solvent-swelling or water-swelling gel or matrix, a reticulated matrix or gel, a membrane, a fibrous support, a porous support and the like. In a particular embodiment, the support is selected among inorganic matrices and polymeric matrices. For instance, supports useful for the invention encompass resins or matrices comprising or consisting in polyoside such as cellulose, carboxymethylcellulose, diethylaminocellulose (DEAE), dextran, cross-linked dextran such as Sephadex®, agarose, cross-linked agarose such as Sepharose®, starches, alginate, chitosan, a synthetic polymer such as polyaminoacids, polyacrylamides, polymers and copolymers based on acrylic acid and derivatives thereof, polyamides, polystyrene, organopolysiloxanes, polyacrylate, polyvinyls polyacrilin, inorganic compounds such as hydroxyapatite, silica or bentonite, and the like. Such supports are commercially available.

For illustration, the enzyme may be entrapped in a polymeric matrix, for instance a matrix of alginate or chitosan. As an alternative, the enzyme may be covalently linked to the support. Typically, the support may contain functional groups able to react directly, or after activation, with an amino acid present in the enzyme so as to create a covalent bound. As another alternative, the enzyme may be absorbed on the support. The interactions between the support and the enzyme may be then stabilized by cross-linking with a bifunctional agent such as glutaraldehyde.

Once prepared, the support comprising the immobilized enzyme having the enzymatic activity of interest can be directly used in the reaction medium. In other words, the support with the immobilized enzyme may be merely added in the reaction medium. When the support is solvent-swelling, the solvent of the reaction may be selected so as to provide an appropriate swelling of the support to render accessible the immobilized enzyme without impairing the catalytic activity of the enzyme.

Alternatively, the enzyme of the invention can be produced in situ, namely in the reaction medium, by a cell able to express said enzyme. The cell may naturally express the enzyme of interest or may have been recombinantly modified to express said enzyme of interest, whereby the cell is a host cell. The methods for introducing a foreign gene and inducing its expression in a host cell are well-known in the prior art. Some examples are provided further below in the section entitled "other objects according to the invention".

In some embodiments, the cell secretes the enzyme of interest in the reaction medium. In other embodiments, the reaction of the invention, namely the reductive amination of the carbonyl-containing compound is performed in cellulo. The cell may be of any type. In some embodiments, the cell is a recombinant prokaryotic or eukaryotic host cell. For instance, the host cell may be any Gram-negative or Gram-positive bacterium useful to produce the enzyme of interest. The host cell may also be a eukaryotic cell such as a mammalian, insect, plant, or fungal cell, in particular yeast cell. Host cells may be selected from *E. coli, Pseudomonas putida, Mycobacterium smegmatis, Corynebacterium glutamicum, Bacillus subtilis, Lactobacillus plantarum, Streptomyces lividans, Acinetobacter baylyi* ADP 1, *Kluyveromyces lactis, Saccharomyces cerevisiae, Pichia pastoris, baculovirus*- and infected insect cells.

In some other or alternate embodiments, the host cell produces, or has been modified to produce, one or several additional enzyme(s) of interest. Said additional enzyme may be helpful for the preparation of the carbonyl-containing compound. For instance, the additional enzyme may be an alcohol dehydrogenase (EC.1.1.1.x) which may be used to prepare the carbonyl-containing compound of formula (I) from the corresponding alcohol. Said additional enzyme may be also selected depending on the final product which is desired. In an additional or alternative embodiment, said additional enzyme may be glucose dehydrogenase or a formate dehydrogenase, said enzymes being useful for the regeneration of the cofactor NAD(P)H.

In some other embodiments, the expression of the enzyme of the invention may be done by in vitro protein expression (also known as in vitro translation, cell-free protein expression, cell-free translation, or cell-free protein synthesis). To that respect, In vitro protein expression systems based on *E. coli*, RRL (Rabbit Reticulose Lysate), wheat germ extracts and insect cells can be used.

The Carbonyl-Containing Compound

As mentioned above, in the method and the use of the invention, the carbonyl-containing compound may be any aldehyde or a ketone, preferably of formula (I) as shown above. $R_1$ and $R_2$ may be such that the molecular weight of the carbonyl-containing compound (or that of the amine of formula (II)) is less than 800 g·mol$^{-1}$, such as less than such as less than 700, 600, 550, 500, 450, 425, 400, 350, 325, 300, 275, 250, 225 or 200 g·mol$^{-1}$. $R_1$ and $R_2$ may be also such there is no carboxyl function at position gamma of the carbonyl group. In certain embodiments, $R_1$ and $R_2$ may be such that the carbonyl-containing compound of formula (I) is also devoid of any carboxyl group at position alpha and/or beta of the carbonyl group.

As mentioned above, $R_1$ and $R_2$ may be independently selected from H, optionally substituted alkyl, optionally substituted heteroalkyl, optionally substituted alkenyl, optionally substituted aryl, optionally substituted heteroaryl, optionally substituted arylalkyl, optionally substituted heteroaryl alkyl, optionally substituted aryl alkenyl, optionally substituted heteroaryl alkenyl, optionally substituted alkyloxy alkyl, optionally substituted heteroaryloxy alkyl, optionally substituted aryloxy alkyl, optionally substituted alkanoyl alkyl with proviso that $R_1$ and $R_2$ are not both H, or $R_1$ and $R_2$ may form together a saturated or unsaturated ring optionally substituted and optionally fused to another ring.

As mentioned above, $R_1$ and $R_2$ forms a ring which can be an hetero-ring, namely comprising one or several heteroatoms such as O, N and S as ring members. Typically, the ring is a 4-7, preferably 5-6-member ring. The ring may be aliphatic. The ring may comprise one or several unsaturations, namely one or several double bonds. The ring may be fused to another ring. Said other ring may be of any type. Typically, the other ring is a 5-7-member ring, which may be aliphatic or aromatic and may contain one or several heteroatoms as ring atoms selected from O, N and S.

When present in the ring formed by $R_1$ and $R_2$, the heteroatom(s) are preferably not at position alpha of the carbonyl group. For instance, the ring formed by $R_1$ and $R_2$ may be selected from cyclohexane, cyclohexene, cyclohexadiene, cyclopentane, cyclopentene, tetrahydropyran, piperidine, tetrahydrothiopyran, pyran, thiopyran and the like.

As mentioned above, $R_1$ and $R_2$ are such that there is no carboxyl group at position gamma of the carbonyl group. In some additional embodiments, $R_1$ and $R_2$ may be such that there is no carboxyl group at position alpha or beta of the carbonyl group.

$R_1$ and $R_2$ may comprise one or several (for instance 2, 3, 4, 5 or 6) substituents. The substituents may be of any type. Possible substituents encompass, without being limited to, $C_1$-$C_6$ alkyl, $C_3$-$C_6$ cycloalkyl, $C_2$-$C_6$ heterocycloalkyl, $C_1$-$C_6$ alkoxy, $C_1$-$C_6$ alkylamino, $C_1$-$C_6$ aminoalkyl, $C_1$-$C_6$ N,N-dialkylamino alkyl, $C_1$-$C_6$ N-alkylamino alkyl, —$N_3$, —F, —I, —Br, —Cl, $C_1$-$C_6$ alkanoyl, $C_1$-$C_6$ acylamino, —$CONH_2$, —$NO_2$, OP(=O)(OH)$_2$, —$SO_3H$, $C_1$-$C_6$ hydroxyalkyl, $C_1$-$C_6$ haloalkyl, $C_1$-$C_6$ alkylthio, $C_2$-$C_{10}$ alkoxy alkyl, $C_2$-$C_6$ alkoxy carbonyloxy, —CN, —$CX_3$ with X is a halogen, preferably F or Cl, —COX with X an halogen, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl. In a particular embodiment, the one or several substituents present in $R_1$ and $R_2$ may be independently selected from OH, $NH_2$, SH, $NO_2$, —CN, halogen, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, $CONH_2$, —C(=O)—R, —NHC(=O)R, —C(=O)NHR, —SC(=O)R, —C(=O)SR, —OC(=O)R, —C(=O)OR, wherein R is a $C_1$-$C_6$ alkyl. and —C(X)$_3$ with X a halogen.

For instance, the one or several substituents are independently selected from OH, $NH_2$, $NO_2$, halogen, $C_1$-$C_4$ alkyl, $C_1$-$C_4$ alkoxy, $C_1$-$C_4$ hydroxyalkyl, and $C_1$-$C_4$ halogenoalkyl.

In a more particular embodiment, the one or more substituents present in $R_1$ and $R_2$ are selected from methyl, ethyl, propyl, isopropyl (iPr), n-butyl, isobutyl, sec-butyl, cyclopropyl, cyclobutyl, —OH, —$OCH_3$, —OEt, —OiPr, $CF_3$, I, Br, Cl and F. For instance, the one or more substituents present in $R_1$ and $R_2$ are selected from methyl, ethyl, propyl, isopropyl, n-butyl, isobutyl, sec-butyl, cyclopropyl, cyclobutyl, —$OCH_3$ and —OH. Appropriate substituents are for instance methyl, ethyl, propyl, isopropyl, OH and —$OCH_3$.

In another embodiment, $R_1$ and $R_2$ are such that: that:
$R_1$ and $R_2$ are independently selected from the group consisting of H, $C_1$-$C_{10}$ alkyl, $C_1$-$C_{10}$ heteroalkyl, $C_2$-$C_{10}$ alkenyl, $C_6$-$C_{12}$ aryl, $C_4$-$C_{12}$ heteroaryl, $C_6$-$C_{14}$ heteroaryl alkyl, $C_7$-$C_{14}$ arylalkyl, $C_8$-$C_{14}$ aryl alkenyl, $C_2$-$C_{10}$ alkyloxy alkyl, $C_7$-$C_{14}$ aryloxy alkyl, $C_5$-$C_{14}$ heteroaryloxy alkyl and $C_2$-$C_{10}$ alkanoyl alkyl, said groups being optionally substituted by one or several substituents selected from OH, $NH_2$, SH, $NO_2$, —CN, halogen, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, —COX, —C(X)$_3$ with X is a halogen, —$CONH_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl, with proviso that $R_1$ and $R_2$ are not simultaneously H, or $R_1$ and $R_2$ form together a saturated or unsaturated 4-7 member ring optionally substituted and optionally fused to another 4-7 member ring, the one or several optional substituents being preferably selected from OH, $NH_2$, SH, $NO_2$, —CN, halogen, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, —COX, —C(X)$_3$ with X is a halogen, an oxo group, —$CONH_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl.

When present, the other ring may be a 5-member ring or a 6-member ring optionally comprising 1 or 2 heteroatoms such as O, N and S as member ring. In some embodiment, the other ring is an aryl or a heteroaryl such as furan, pyrrole, thiophene, imidazole, oxazole, thiazole, phenyl and pyridine.

For instance, $R_1$ and $R_2$ can form together an indane ring so that the carbonyl-containing group is an indanone.

In an additional embodiment, $R_1$ and $R_2$ are such that:
$R_1$ and $R_2$ are independently selected from the group consisting of H, $C_1$-$C_{10}$ alkyl, $C_2$-$C_{10}$ alkenyl, $C_6$-$C_{12}$ aryl, $C_7$-$C_{14}$ arylalkyl, and $C_8$-$C_{14}$ arylalkenyl, said groups being optionally substituted by one or several substituents selected from OH, $NH_2$, SH, $NO_2$, —CN, halogen, $C_1$-$C_4$ alkyl, $C_1$-$C_4$ alkoxy, $C_1$-$C_4$ hydroxyalkyl, $C_1$-$C_4$ halogenoalkyl, $C_1$-$C_4$ aminoalkyl, —C(X)$_3$ with X a halogen, $CONH_2$, —C(=O)—R, —NHC(=O)R, SC(=O)R, —C(=O)SR, —C(=O)NHR, —OC(=O)R, and —C(=O)OR, wherein R is a $C_1$-$C_4$ alkyl, with proviso that $R_1$ and $R_2$ are not simultaneously H, or $R_1$ and $R_2$ forms together a ring such that the carbonyl-containing compound is of formula (Ia):

(Ia)

wherein n is an integer selected from 0, 1 or 2, ===== means a double or a single bound, and $R_4$ is a substituent selected from H, $C_1$-$C_4$ alkyl, —OH, $NH_2$, SH, $NO_2$, —CN, halogen, $C_1$-$C_4$ alkoxy, $C_1$-$C_4$ hydroxyalkyl, $C_1$-$C_4$ halogenoalkyl, $C_1$-$C_4$ aminoalkyl, an oxo group, —C(X)$_3$ with X is a halogen, $CONH_2$, —C(=O)—R, —NHC(=O)R, —C(=O)NHR, SC(=O)R, —C(=O)SR —OC(=O)R, and —C(=O)OR, wherein R is a $C_1$-$C_4$ alkyl. $R_4$ may be at any position of the ring.

In another embodiment, $R_1$ and $R_2$ are such that
$R_1$ and $R_2$ are independently selected from H, phenyl, $C_1$-$C_{10}$ alkyl and $C_1$-$C_{10}$ alkenyl, said phenyl, $C_1$-$C_{10}$ alkyl and $C_1$-$C_{10}$ alkenyl being optionally substituted by one or several substituents selected from OH, $C_1$-$C_4$ alkyl, $C_1$-$C_4$ alkoxy, and $C_1$-$C_4$ hydroxyalkyl, with proviso that $R_1$ and $R_2$ are not simultaneously H, or $R_1$ and $R_2$ forms together a ring such that the carbonyl-containing compound is of formula (Ia):

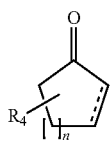
(Ia)

wherein n is 0 or 1 and $R_4$ is selected from H, $C_1$-$C_4$ alkyl, —OH, $C_1$-$C_4$ alkoxy, and $C_1$-$C_4$ hydroxyalkyl.

For instance, $R_1$ and $R_2$ may be such that:

$R_1$ and $R_2$ are independently selected from H, phenyl, $C_1$-$C_6$, preferably $C_1$-$C_4$, alkyl and $C_1$-$C_6$, preferably $C_1$-$C_4$, alkenyl, said groups being optionally substituted by a substituent selected from OH and $C_1$-$C_3$ alkyl, preferably methyl, with proviso that $R_1$ and $R_2$ are not simultaneously H, or $R_1$ and $R_2$ forms together a ring such that the carbonyl-containing compound is of formula (Ia):

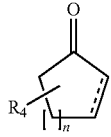

Wherein n is 1 or 2, ===== means a double or a single bound, and $R_4$ is H or a $C_1$-$C_3$ alkyl, preferably methyl. $R_4$ may be at any position of the ring.

For illustration only, $R_1$ and $R_2$ may be such that:

$R_1$ and $R_2$ are independently selected from H, phenyl, $C_1$-$C_4$ alkyl and $C_1$-$C_4$ alkenyl, said $C_1$-$C_4$ alkyl and $C_1$-$C_4$ alkenyl being optionally substituted by a substituent selected from OH and $C_1$-$C_3$ alkyl with proviso that $R_1$ and $R_2$ are not simultaneously H, or $R_1$ and $R_2$ forms together a ring such that the carbonyl-containing compound is of formula (Ia):

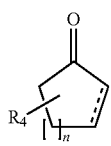

Wherein n is 1 or 2, ===== means a double or a single bound, and $R_4$ is H or a $C_1$-$C_3$ alkyl. $R_4$ may be at any position of the ring.

Source of Nitrogen

In the method of the invention, a source of nitrogen is present in the reaction medium to allow the reductive amination of the carbonyl-containing compound to occur. Sources of nitrogen are usually organic or inorganic nitrogen compounds such as ammonia salts, ammonia gas, or amino compounds. Typically, the source of nitrogen is a compound of formula $R_3$—$NH_2$ or a salt thereof. The group $R_3$ may be selected from H, alkyl, alkenyl, alkynyl, and aryl, said groups being optionally substituted. In some embodiments, $R_3$ is selected from H, $C_1$-$C_{10}$ alkyl, $C_2$-$C_{10}$ alkenyl, $C_2$-$C_{10}$ alkynyl and $C_6$-$C_{14}$ aryl, optionally substituted by one or several substituents selected from OH, $C_1$-$C_3$ alkyl, $C_1$-$C_3$ alkoxy, $NH_2$ and halogens. In an another embodiments, $R_3$ is selected from H and $C_1$-$C_3$ alkyl such as methyl. Appropriate $R_3$ are H and $CH_3$—.

Preferably $R_3$ is H. In other words, the carbonyl-containing compound of formula (I) is contacted with enzyme of the invention in the presence of ammonia or a source of ammonia. In such an embodiment, sources of ammonia typically include ammonia and ammonium salts such as ammonium formate, ammonium sulfate, ammonium chloride, ammonium hydroxide, ammonium acetate, ammonium phosphate, ammonium carbonate, and combinations thereof. When the nitrogen source is ammonia and/or ammonium salt, $R_3$ is H and the resulting amine is a primary one of formula:

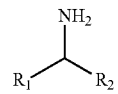

$R_1$ and $R_2$ being as defined above.

The Resulting Amine Compound of Formula (II)

The resulting amine is of formula (II):

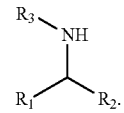
(II)

$R_1$ and $R_2$ is as defined for the corresponding carbonyl-containing compound.

It goes without saying that when the carbonyl-containing compound is of formula (Ia), the amine is of formula (IIa):

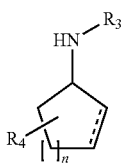
(IIa)

wherein $R_4$ and n are as defined above.

$R_3$ is function of the nitrogen source used in the method of the invention. In preferred embodiments, $R_3$ is H. Thus, the resulting amine is preferably a primary amine. The table 1 hereunder shows examples of amines prepared by the method of the invention, the source of nitrogen being an ammonium salt:

| Carbonyl-containing compound of formula (I) | Resulting amine of formula (II) |
|---|---|
| 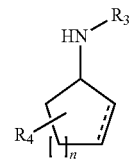 | |

-continued

| Carbonyl-containing compound of formula (I) | Resulting amine of formula (II) |
|---|---|

[Chemical structures showing pairs of carbonyl compounds and their corresponding amines, including: 3-methylcyclohexanone/3-methylcyclohexylamine, 4-methylcyclohexanone/4-methylcyclohexylamine, 3,5-dimethylcyclohexanone/3,5-dimethylcyclohexylamine, 1-cyclohexylethanone/1-cyclohexylethylamine, cyclohex-2-enone/cyclohex-2-enylamine, cyclopentanone/cyclopentylamine, 2-methylcyclopentanone/2-methylcyclopentylamine, 3-methylcyclopentanone/3-methylcyclopentylamine, pentan-3-one/pentan-3-amine, hexan-3-one/hexan-3-amine, pentan-2-one/pentan-2-amine, methyl vinyl ketone/corresponding amine, 1-hydroxypropan-2-one/1-hydroxypropan-2-amine, pentanal/pentan-1-amine, 2-methylbutanal/2-methylbutan-1-amine, isobutyraldehyde/isobutylamine, 3-methylbutan-2-one/3-methylbutan-2-amine, 4-hydroxybutan-2-one/4-hydroxybutan-2-amine, benzaldehyde/benzylamine, indanone/1-aminoindane]

When the carbonyl-containing compound is a pro-chiral ketone, e.g. instance when $R_1$ and $R_2$ are different, the carbon bearing the amino group in the amine of formula (II) is asymmetric. In other words, the resulting amine may exist in two enantiomers or several diastereoisomers.

Without to be bound by any theory, the Inventors is of the opinion that the method of the invention is enantio- or diastereo-selective, which means that one enantiomer or one diastereomer of the amine is formed in preference to another. In some embodiments, said diastereomer or said enantiomer represents more than 50%, preferably more than 60%, 70%, 80%, 90%, 95% or 98% by mole of the resulting amine, the percentage referring to the total molar amount of amine formed by the reductive amination of carbonyl-containing compound according to the invention. In other words, the enzyme used in the method of the invention may be enantioselective and/or diastereoselective.

For example, the amine resulting from the reductive amination of pentan-2-one by the enzyme of SEQ ID NO:1 or SEQ ID NO:2 is (S)-2-aminopentane with an enantiomeric excess of 98% (which means that 99% by mole of the resulting 2-aminopentane is the enantiomer (S)). As a further example, the amine resulting from the reductive amination of 2-methylcyclohexanone with the enzyme of SEQ ID NO:1 or SEQ ID NO:2 is a diastereoisomer wherein the carbon bearing the amino group is of (S)-configuration with an enantiomeric excess of 91% and 99%, respectively.

Conditions to Implement the Reaction

As mentioned above, the enzyme of the invention may be used in any appropriate forms, in particular those described herein. The enzyme may be provided in a free state, for example in an isolated form, in an enriched form, in a purified form or in a semi-purified form. For instance, said enzyme may be present in a supernatant or in a supernatant extract recovered from a culture medium. The enzyme may be also provided as a cell lysate. Alternatively, the enzyme may be formulated in a composition. In some embodiments, the enzyme is immobilized on a support as described herein. In some other embodiments, the enzyme may be expressed in situ by a host cell, or by a cell which is able to endogenously express said enzyme.

In some embodiments, the method of the invention comprises:
(a) providing a product selected among the group consisting of an enzyme of the invention, namely having the RedAm activity and comprising a polypeptide having at least 50% of sequence identity with an amino acid sequence selected from SEQ ID NO:1, SEQ ID NO:2, SEQ ID NO:3, SEQ ID NO:4, SEQ ID NO:5 and SEQ ID NO:6, a composition comprising said enzyme, a support on which an said enzyme is immobilized, and a cell or a host cell able to express said enzyme, or a cell lysate thereof,
(b) contacting the product provided in step (a) with the carbonyl-containing compound of formula (I) as described above, in the presence of a cofactor selected from NADPH, NADH, combinations thereof and synthetic analogs thereof and a source of nitrogen, so as to promote the reductive amination of the carbonyl-containing compound by the product provided in step (a), and
(c) optionally recovering and/or purifying the resulting amine formed in step (b).

The running conditions may vary, among others, depending on the source of the enzyme which is used. When the enzyme is used in a purified or semi-purified form or in an immobilized form, the pH, the temperature and the solvent are selected so as to promote the enzymatic activity. When the enzyme is expressed in situ by a cell or a host cell, the running conditions may be conducive for the expression of the enzyme by said cell or host cell.

In some embodiments, the method of the invention is performed by adding the enzyme of the invention in the reaction medium. Typically, the enzyme is contacting with the carbonyl-containing compound in conditions suitable for the enzyme activity. The enzyme may be in free state or immobilized on an appropriate support. The reaction medium comprises a source of nitrogen, a cofactor, typically NADH and/or NADPH, and optionally other ingredients, for instance for stabilizing the enzyme or promoting the activity of the enzyme. Alternatively, the cofactor may be a synthetic analog of NAD(P)H. Such analogs encompass, without being limited to methyl-1,4-dihydronicotinamide (MNAH), 1-benzyl-1,4-dihydronicotinamide (BNAH) or its para-methoxy derivative (p-MeO-BNAH) (C. E. Paul et al., *Appl. Microbiol. Biotechnol,* 2016, 100, 4773-4778).

The reaction medium is typically liquid. It may be homogeneous or non-homogeneous. In some embodiments, the reaction medium is a monophasic phase, preferably an aqueous phase. In other embodiments, the reaction medium is biphasic and comprises an aqueous phase and an organic phase. Thus, the reaction medium typically consists of, or comprises, an aqueous phase. This aqueous phase may be a buffered aqueous solution. The pH of the buffered aqueous solution is typically from 6.5 to 11.0, for instance from 7.5 to 10.9. Any type of buffer enabling to obtain the desired pH and compatible with the enzyme of the invention can be used.

When $R_3NH_2$ is $NH_3$, one can use a buffer comprising a source of ammonia such as ammonium-based buffer, e.g. ammonium formate buffer or ammonium chloride-ammonium hydroxide buffer.

The cofactor(s) are added in the aqueous phase. Optionally, a system enabling to generate/regenerate NADPH, NADH or synthetic analogs thereof may be present in the aqueous phase. Such a system encompasses for instance glucose/glucose dehydrogenase (GDH) system in which GDH oxidizes glucose into gluconate while simultaneously reduces NAD(P)+ into NAD(P)H. An example of GDH is for instance the GDH from *Bacillus subtilis* deposited in Genbank under AAA22463. Another possible system is glucose-6P/glucose-6P dehydrogenase (G6PDH) in which G6PDH oxidizes glucose-6P into 6-phospho-D-gluconate while simultaneously reduces NAD(P)+into NAD(P)H. An example of G6PDH is for instance the G6PDH from *Leuconostoc mesenteroides* or *Saccharomyces cerevisiae*. Another possible system is formate/formate dehydrogenase, the formate dehydrogenase (FDH) catalyzing the oxidation of formate to $CO_2$ while reducing NAD(P)+ into NAD(P)H. An example of FDH is for instance FDH from *Candida boidinii* deposited in Uniprot under O13437. Another possible system is phosphite/phosphite dehydrogenase (PTDH), the PTDH catalyzing the oxidation of phosphite to phosphate while reducing NAD(P)+ into NAD(P)H. Another possible system is alcohol/alcohol dehydrogenase (ADH) system in which ADH oxides an alcohol, for instance isopropyl alcohol, into the corresponding carbonyl compound, for instance acetone.

Depending on its solubility, the carbonyl-containing compound may be firstly dissolved in an appropriate co-solvent such as DMF, THF or DMSO and then added in the monophasic reaction medium. The organic solvent may account for 0.1% to 50%, preferably from 0.1% to 20% per volume of the aqueous phase.

When a biphasic reaction medium is used, the carbonyl-containing compound is at least partially present in the organic phase. The organic phase is typically composed of a solvent with a limited miscibility with water such alkanes e.g. as heptane, hexane, octane, halogenoalkanes e.g. chloroform or dichloromethane, aromatic compounds e.g. toluene, esters e.g. as ethyl acetate, isopropyl acetate or butyl acetate, or ethers e.g. methyl-tert-butyl ether.

The reagents, namely the enzyme, the carbonyl-containing compound, the cofactor, and the source of nitrogen, can be added in any order in the reaction medium. Preferably, the carbonyl-containing compound and then the enzyme are added. The source of nitrogen may be introduced in stoechiometric excess. The cofactor(s) may be also present in stoechiometric excess, when no regeneration system is used, The molar ratio of $R_3NH_2$ to the carbonyl-containing compound may be from 1 to 500, typically from 1 to 100.

For instance, if $R_3$ is H, the source of nitrogen is typically an ammonium salt which may be present at a concentration from 10 mM to 5 M. For illustration only, the cofactor may be present at a concentration from 50 μM to 500 M, if a regeneration system is present in the medium, and the carbonyl-containing compound may be present at a concentration from 0.5 mM to 1 M. The enzyme is added in an appropriate amount.

The reaction medium may be stirred, at a suitable temperature, for instance from 20° C. to 40° C. during a sufficient reaction time. The resulting amine of formula (II) may be then recovered. In other embodiments, the enzyme is produced in situ or in cellulo by a whole cell. The cell may be a wild-type cell which endogenously expresses the enzyme of the invention. Alternatively, the cell may be a host cell recombinant for said enzyme. Examples of appropriate wild-type cells or host cells are described above and below, respectively.

Thus, the invention also relates to a method for producing an amine compound from a carbonyl-containing compound of formula (I) comprising the steps of:
cultivating a cell capable of expressing an enzyme which has a RedAm activity and comprises a polypeptide having at least 50% of sequence identity with an amino acid sequence selected from the group consisting of SEQ ID NO:1, SEQ ID NO:2, SEQ ID NO:3, SEQ ID NO:4, SEQ ID NO:5, and SEQ ID NO:6 in conditions conducive for the expression of said enzyme,
contacting the cell with a carbonyl-containing compound of formula (I), and
optionally recovering the resulting amine compound from the medium.

The cell can be cultivated continuously or discontinuously in the batch process or in the fed batch or repeated fed batch process. The culture medium is selected so as to satisfy the requirements of the particular strain used in the method of the invention. The culture medium that can be used according to the invention generally comprises one or more sources of carbon, sources of nitrogen, inorganic salts, vitamins and/or trace elements. Suitable media are available from commercial suppliers or may be prepared according to published compositions (e.g., in catalogues of the American Type Culture Collection).

The carbonyl-containing compound, and if needed the source of $R_3NH_2$ and NADPH and/or NADH are present or added in the culture medium. Alternatively, the cells are recovered from the culture medium before being contacted with the carbonyl-containing compound in an appropriate medium for the cells and the enzymatic reaction to occur.

Additional Steps of the Method According of the Invention

The method of the invention may comprise one or several additional steps. For instance, the method of the invention may comprise a step of recovering the amine of formula (II). The method may also comprise a step of purifying said amine of formula (II). Said compound may be purified by any method of purification known in the art such as precipitation, filtration, extraction, preparative chromatography, recrystallization and combinations thereof. In some particular embodiments, a chiral chromatography may be performed in order to eliminate unwanted stereoisomers optionally present. The method of the invention may also comprise a step of recovering the enzyme, once the reaction is achieved.

The method of the invention may also comprise one or several steps prior to the step of contacting the carbonyl-containing compound with the enzyme of the invention. For instance, the method may comprise a step of producing the enzyme of the invention. Typically, the enzyme of the invention may be prepared by any conventional methods, for instance by expression in a host cell or in a wild-type cell capable of expressing such an enzyme, followed by the purification of said enzyme.

As another example, the method of the invention may comprise a step of providing the carbonyl-containing compound. The carbonyl-containing compound may be prepared from the corresponding alcohol by chemical oxidation or enzymatic oxidation, for instance by using an alcohol dehydrogenase (ADH) (E.C.1.1.1.x) as shown in WO2016/001362, the disclosure of which being incorporated herein by reference.

Thus, in a particular embodiment, the invention comprises a step of preparing the carbonyl-containing compound of formula (I) by contacting an alcohol of formula $R_1$—CHOH—$R_2$, wherein $R_1$ and $R_2$ are as defined in formula (I) with an alcohol dehydrogenase in the presence of $NADP^+$ and/or $NAD^+$ cofactor. The method of the invention may be performed in one pot, namely the oxidation of the alcohol into the carbonyl-containing compound and the amination of the carbonyl-containing compound into the desired amine compound are performed in the same reaction medium (ADH/RedAm cascade).

Uses of the Amine Obtained by the Method of the Invention

The resulting amines can be used as bulk chemicals or intermediate of thereof, or as building blocks for the synthesis of a molecule of interest, such as pharmaceutical active ingredients, agrochemical active ingredients, polymers and the like. Indeed, the amine resulting from the method of invention may comprise at least one asymmetric carbon, and thus can be used as chiral synthons.

Thus, the invention also relates to method for producing a compound of interest, which comprises the steps of:
Preparing an amine of formula (II) by the method of the invention
Preparing the compound of interest from the resulting amine.

The compound of interest may be of any type. For instance, the compound of interest is a pharmaceutical active ingredient comprising a chiral amine moiety or a chiral amine building block for the preparation of a pharmaceutical active ingredient. Alternatively, the compound of interest may be a primary amine useful in bulk chemistry.

Other Objects According to the Invention

The invention also relates to an enzyme having an RedAm activity and comprising a polynucleotide having at least 50%, e.g. at least 55%, 60%, 65%, 70%, 75%, 80%, 85%, 90% or 95% of sequence identity with an amino sequence selected from SEQ ID NO:1, SEQ ID NO:2, SEQ ID NO:3 SEQ ID NO:4, SEQ ID NO:5 and SEQ ID NO:6, preferably SEQ ID NO:1,SEQ ID NO:2, SEQ ID NO:3, SEQ ID NO:4 and SEQ ID NO:5.

The present invention also relates to a polynucleotide encoding an enzyme of the present invention. The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known by the one skilled in the art, including chemical synthesis, recombination, and mutagenesis.

A polynucleotide encoding an enzyme of the invention may be selected from the group consisting of:
a nucleic acid that encodes an enzyme having a RedAm activity and comprising a polypeptide having at least 50%, e.g. at least 60%, 70%, 75%, 80%, 85%, 90% or 95% of sequence identity with an amino sequence selected from SEQ ID NO:1, SEQ ID NO:2, SEQ ID NO:3, SEQ ID NO:4, SEQ ID NO:5 and SEQ ID NO:6, a nucleic acid that encodes for a variant of an enzyme of amino acid sequence selected from SEQ ID NO:1, SEQ ID NO:2, SEQ ID NO:3,SEQ ID NO:4, SEQ ID NO:5 and SEQ ID NO:6, said variant having a RedAm, and a nucleic acid comprising a sequence selected from SEQ ID NO:7, SEQ ID NO:8, SEQ ID NO:9, SEQ ID NO:10, SEQ ID NO:11 and SEQ ID NO:12 and an optimized version thereof.

The present invention also relates to nucleic acid constructs comprising a polynucleotide encoding an enzyme according to the present disclosure operably linked to one or more control sequences that direct the expression of the coding sequence in a suitable host cell under conditions compatible with the control sequences.

In some embodiments, the control sequence(s) is/are heterologous to the polynucleotide encoding the enzyme of the invention.

A polynucleotide may be manipulated in a variety of ways to provide for expression of the enzyme. Manipulation of the polynucleotide prior to its insertion into a vector may be desirable or necessary depending on the expression vector. The techniques for modifying polynucleotides utilizing recombinant DNA methods are well known in the art.

The control sequence may include a promoter that is recognized by a host cell or an in vitro expression system for expression of a polynucleotide encoding an enzyme of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell.

For illustration only, examples of suitable promoters in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cry111A gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25).

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention. For instance, terminators for bacterial host cells may be obtained from the genes for *Bacillus clausii* alkaline protease (aprH), *Bacillus licheniformis* alpha-amylase (amyL), and *Escherichia coli* ribosomal RNA (rrnB).

The control sequence may be also an mRNA stabilizer region downstream of a promoter and upstream of the coding sequence of a gene which increases expression of the gene.

The control sequence may also be a leader, a non-translated region of an mRNA that is important for translation by the host cell. The leader is operably linked to the 5'-terminus of the polynucleotide encoding the enzyme. Any leader that is functional in the host cell may be used. The control sequence may also be a polyadenylation sequence, a sequence operably linked to the 3'-terminus of the polynucleotide encoding the enzyme and, when transcribed, is recognized by the host cell as a signal to add polyadenosine residues to transcribed mRNA. Any polyadenylation sequence that is functional in the host cell may be used.

The control sequence may also be a signal peptide coding region that encodes a signal peptide linked to the N-terminus of the enzyme and directs the enzyme into the cell's secretory pathway. The 5'-end of the coding sequence of the polynucleotide may inherently contain a signal peptide coding sequence naturally linked in translation reading frame with the segment of the coding sequence that encodes the enzyme. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used. For illustration only, effective signal peptide coding sequences for bacterial host cells encompass the signal peptide coding sequences obtained from the genes for *Bacillus* NCIB 1 1837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

The present invention also relates to recombinant expression vectors comprising a nucleic acid construct as disclosed above, or a polynucleotide encoding an enzyme of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the enzyme at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication.

The vector may contain one or more selectable markers that permit easy selection of transformed, transfected, transduced, or the like cells. Examples of bacterial selectable markers are genes that confer antibiotic resistance such as ampicillin, chloramphenicol, kanamycin, neomycin, spectinomycin, or tetracycline resistance, resistance to heavy metals and the like.

The vector preferably contains an element(s) that permits integration of the vector into the host cell's genome or autonomous replication of the vector in the cell independent of the genome.

When integration into the host cell genome occurs, integration of the sequences into the genome may rely on homologous or non-homologous recombination. Alternatively, the vector may contain additional polynucleotides for directing integration by homologous recombination into the genome of the host cell at a precise location(s) in the chromosome(s). The integrational elements may be any sequence that is homologous with the target sequence in the genome of the host cell. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell.

The selection of the above elements depends on the host cell in which the expression is desired. The methods for selecting these elements are well known by the skilled artisan. The vectors may be constructed by classical techniques of molecular biology well known by the skilled artisan.

Host Cells

The present invention also relates to recombinant host cells, comprising a polynucleotide encoding the enzyme according to the present disclosure operably linked to one or more control sequences that direct the production of the enzyme of the present invention. A construct or vector comprising a polynucleotide encoding the enzyme of according to the present disclosure is introduced into a host cell so that the construct or vector is maintained as a chromosomal integrant or as a self-replicating extra-chromosomal vector. The term "host cell" encompasses any progeny of a parent cell that is not identical to the parent cell due to mutations that occur during replication. The choice of a host cell depends upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Mycobacterium smegmatis, Bacillus, Clostridium, Corynebacterium, Enterococcus, Geobacillus, Lactobacillus, Lactococcus, Oceanobacillus, Staphylococcus, Streptococcus*, and *Streptomyces*. Gram-negative bacteria include, but are not limited to, *Acinetobacter, Campylobacter, E. coli, Flavobacterium, Fusobacterium, Helicobacter, Ilyobacter, Neisseria, Pseudomonas, Salmonella*, and *Ureaplasma*.

The introduction of nucleic acid, expression cassette or vector of the invention into the host cell may be performed by any appropriate methods such as protoplast transformation, competent cell transformation, electroporation, transduction, conjugation, protoplast fusion, or transfection such as chemically-mediated transfection or liposome-mediated transfection. The technique to use depends on the microorganism host cell. These techniques are well-known by the skilled artisan. The host cell may be transformed, transduced or transfected in a transient or stable manner.

The host cell may also be a eukaryote, such as a mammalian, insect, plant, yeast or fungal cell, in particular yeast cell and fungal cell. For instance, the yeast host cell may be a *Candida, Hansenula, Kluyveromyces, Pichia, Saccharomyces, Schizosaccharomyces*, or *Yarrowia* cell. The host cell may be a filamentous fungal cell such as *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *richoderma* cell. The cell may be also a mammalian cell. In such a case, it goes without saying that the cell is a non-human and non-embryonic cell. In addition, the enzyme of the invention could be produced by a non-human transgenic animal, for instance in the milk produced by the animal, or by a transgenic plant.

Method of Production of the Enzyme

The present invention also relates to methods for producing the enzyme of the present invention by using a cell which naturally expresses the enzyme of the invention or by using a host cell according to the invention.

In a more specific aspect, the invention relates to a method for producing an enzyme having a RedAm activity and comprising a polypeptide having at least 50% of sequence identity with an amino acid sequence selected from the group consisting of SEQ ID NO:1, SEQ ID NO:2, SEQ ID NO:3 SEQ ID NO:4, SEQ ID NO:5 and SEQ ID NO:6, said method comprising the steps of:

cultivating a cell, which in its wild-type form is capable of producing the enzyme, or a recombinant host cell of the invention, in conditions conducive for production of the enzyme, and recovering and/or purifying the enzyme.

It goes without saying that the enzyme may have one or several features as fully-described in the above section entitled "enzyme to implement the method od the invention".

The cell is cultivated in a nutrient medium suitable for production of the enzymes of the invention using methods known in the art. For example, the cell may be cultivated by shake flask cultivation, or small-scale or large-scale fermentation (including continuous, batch, fed-batch, or solid state fermentations) in laboratory or industrial fermenters performed in a suitable medium and under conditions allowing the enzyme to be expressed and/or isolated. The cultivation may take place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the enzyme is secreted into the nutrient medium, the enzyme can be recovered directly from the medium. If the enzyme is not secreted, it can be recovered from cell lysates. The enzyme may be detected using methods known in the art that are specific for the enzyme. These detection methods include, but are not limited to, use of specific antibodies, detection of tag, formation of an enzyme product, or disappearance of an enzyme substrate. For example, an enzyme assay may be used to determine the activity of the enzyme.

The enzyme may be recovered using methods known in the art. For example, the enzyme may be recovered from the nutrient medium by conventional procedures including, but not limited to, collection, centrifugation, filtration, extraction, spray-drying, evaporation, and/or precipitation.

The enzyme may be purified by a variety of procedures known in the art including, but not limited to, chromatography (e.g., ion exchange, affinity, hydrophobic, and size exclusion), electrophoretic procedures (e.g., preparative isoelectric focusing), differential solubility (e.g., ammonium sulfate precipitation), SDS-PAGE, or extraction to obtain substantially pure enzyme. In an alternative aspect, the enzyme is not recovered, but rather a host cell of the present invention expressing the enzyme, or a lysate thereof, is used as a source of the enzyme.

Supports, Compositions and Kits of the Invention

The enzyme of the invention may be immobilized on a support. The present invention thus relates to a support on which an enzyme of the invention is immobilized. The invention further relates to a method for preparing such a support comprising the step of providing an enzyme according to the invention and immobilizing said enzyme on a support. The enzyme of the invention may be immobilized by any appropriate method described in the state in the art, for instance, by covalent binding, adsorption, entrapment or membrane confinement. It goes without saying that the enzyme of the invention still displays the RedAm activity once immobilized.

Supports of interest are described above in the section relating to the enzyme of the invention. Once prepared, the support of the invention can be directly used in a reaction medium. In other words, the support of the invention may be merely added in the reaction medium. When the support is solvent-swelling, the solvent of the reaction may be selected so as to provide an appropriate swelling of the support to render accessible the immobilized enzyme without impairing the catalytic activity of the enzyme. As an alternative, the support can be used to prepare a reactor, which can be for instance an enzyme reactor, a membrane reactor, a continuous flow reactor such as a stirred tank reactor, a continuously operated packed bed reactor, or a continuously operated fluidized bed reactor, or a packed bed reactor.

In some embodiments, the support of the invention is recyclable and may be used several times in a row.

The enzyme of the invention can be also formulated in a composition. A further aspect of the invention is thus a composition comprising an enzyme of the invention and an excipient. The composition may be liquid or dry, for instance in the form of a powder. In some embodiments, the composition is a lyophilizate. The enzyme may be present in a purified or in an enriched form. Appropriate excipients encompass buffers commonly used in biochemistry, agents for adjusting pH, antioxidant, redox agent such as dithiothreitol, preservatives such as sodium benzoate, sodium sorbate or sodium ascorbate, conservatives, protective or stabilizing agents such as starch, malodextrin, arabic gum, salts, sugars e.g. sorbitol, trehalose or lactose, glycerol, polyethyleneglycol, polyethene glycol, polypropylene glycol, propylene glycol, sequestering agent such as EDTA, amino acids, a carrier such as a solvent or an aqueous solution, and the like. The composition of the invention may comprises from 1% to 99%, preferably from 10% to 95% by weight of an enzyme of the invention and from 1% to 99%, preferably from 5% to 90% by weight of excipient(s). The composition of the invention may be obtained by mixing the enzyme with one or several excipients.

In a further aspect, the invention relates to a kit comprising:
an enzyme of the invention, or
a composition comprising an enzyme of the invention, or
a support of the invention, or
a host cell able to express an enzyme of the invention as described above.

Said kit is preferably dedicated for implementing a method of the invention such as those described hereunder, especially a method for preparing an amine from a carbonyl-containing compound of formula (I). The kit may further comprise:
reagent(s) such as one or several carbonyl-containing compound of formula (I), a buffer, a source of nitrogen, e.g. an ammonium salt, and NADPH and/or NADH, and/or
compounds required for culturing the host cell such as nutrients, a culture medium, a mean for assessing the growth of the host cell, and the like, and/or
a mean for detecting or quantifying the progress of the enzymatic reaction, and/or
written instructions, for instance, relating to the running conditions for implementing the method, in particular the pH and the temperature to use.

The present invention also relates to a kit for preparing a support of the invention, said kit comprising an enzyme of the invention and at least one of the following items:
a support for the immobilization of the enzyme, and/or
a reagent for immobilizing the enzyme of the invention on said support and/or
written instructions, for instance, relating to the running conditions for immobilizing the enzyme on the support.

Other Methods and Uses of the Invention

It goes without saying that the instant invention also relates to the use of an enzyme having a reductive aminase activity and preferably comprising a polypeptide having at least 50% of sequence identity with an amino acid sequence selected from SEQ ID NO:1, SEQ ID NO:2, SEQ ID NO:3, SEQ ID NO:4, SEQ ID NO:5 and SEQ ID NO:6 to catalyze the reverse reaction, namely the oxidative deamination of an amine compound of formula (II) into a containing-carbonyl compound of formula (I).

In other words, the invention also relates to the use of an enzyme having a reductive aminase (RedAm) activity and comprising a polypeptide having at least 50% of sequence identity with an amino acid sequence selected from SEQ ID NO:1, SEQ ID NO:2, SEQ ID NO:3, SEQ ID NO:4, SEQ ID NO:5 and SEQ ID NO:6, as a catalyst, in the oxidative deamination of a primary or secondary amine preferably devoid of any carboxyl group at position gamma of the amino group. In certain embodiments, the primary or secondary amine may be devoid of any carboxyl group at position alpha and beta of the amino group.

The invention also relates to a method for preparing a carbonyl-containing compound of formula (I) by contacting an amine compound of formula (II) with the enzyme of the invention in the presence of NAD+ and/or NADP+ and/or a synthetic analog thereof. It goes without saying that the enzyme of the invention, the amine of formula (II) and the carbonyl-containing compound of formula (I) are as described above in any one of the embodiments of the invention. The enzyme of the invention can be provided in any form, as described above, e.g. as a purified enzyme, a cell lysate, a cell-free extract, a cell supernatant, a support-immobilized enzyme or may be produced in situ or in cellulo by a wild-type cell or a recombinant cell able to express the enzyme of the invention.

A further object of the invention is the use of an enzyme having a reductive aminase (RedAm) activity and comprising a polypeptide having at least 50% of sequence identity with an amino acid sequence selected from SEQ ID NO:1, SEQ ID NO:2, SEQ ID NO:3, SEQ ID NO:4, SEQ ID NO:5 and SEQ ID NO:6, as a catalyst, in the reduction of a imine or iminium ion into a amine or a salt thereof. The invention also relates to a method for preparing a amine by contacting a imine or a iminium salt with the enzyme of the invention in the presence of a cofactor selected from NADH, NADPH, a synthetic analog thereof or a combination thereof.

In some embodiments, the imine or the iminium is cyclic.

In other embodiments, the imine is a compound of formula (III):

(III)

or a salt thereof,
wherein $R_1$, $R_2$ and $R_3$ are as defined herein, in any embodiment of the compound of formula (I) and compound of formula (II).

Further aspects and advantages of the present invention will be disclosed in the following experimental section, which should be regarded as illustrative and not limiting the scope of the present application.

LIST OF SEQUENCES

| SEQ ID NO: | Enzymes |
|---|---|
| 1 | Enzyme of Uniprot code A0A0D6I8P6 from *Mycobacterium smegmatis* |
| 2 | Enzyme of Uniprot code S9Q235 from *Cystobacter fuscus* DSM 2262 |
| 3 | Enzyme of Uniprot code C3UMY1 from *Microbacterium* sp. MA1 |
| 4 | Enzyme of Uniprot code E3CZE3 from *Aminomonas paucivorans* DSM 12260 |
| 5 | Enzyme of Uniprot code K0UKT5 from *Mycobacterium vaccae* ATCC 25954 |
| 6 | Enzyme of Uniprot code A0A101AWU7 from *Mycobacterium* sp. GA-2829 |
| 7 | Coding sequence (ADNc) of SEQ ID NO:1 |
| 8 | Coding sequence (ADNc) of SEQ ID NO:2 |
| 9 | Coding sequence (ADNc) of SEQ ID NO:3 |
| 10 | Coding sequence (ADNc) of SEQ ID NO:4 |
| 11 | Coding sequence (ADNc) of SEQ ID NO:5 |
| 12 | Coding sequence (ADNc) of SEQ ID NO:6 |

EXAMPLES

Cloning, Production and Purification of Enzymes

Primers were chosen, genes were cloned and protein overexpressed in *E. coli* as previously described (Vergne-Vaxelaire et al., Adv. Synth. Catal. 2013, 355, 1763-1779) excepting for SEQ ID NO:6 for which the gene was synthezised externally and cloned with a poly-histidine tag in C-ter position as the enzyme resulting from a cloning in N-ter position showed no activity in the tested conditions.

Each expression plasmid was transformed into *E. coli* (for example *E. coli* BL21-CodonPlus (DE3)-RIPL). Cell culture, isopropyl b-D-thiogalactopyranoside (IPTG) induction of protein production and cell lysis were conducted as previously published (C. Guérard-Hélaine et al. ChemCatChem 2015, 7, 1871-1879). The resulting cell lysate preparations were used to detect reductive aminase activity or the reverse deamination reaction. Purifications for enzymes of SEQ ID NO:1 and SEQ ID NO:2 were obtained from a 400-ml culture as described (A. Kreimeyer et al., J. Biol. Chem. 2007, 282, 7191). Enzymes of SEQ ID NO:3, SEQ ID NO:4, SEQ ID NO:5 and SEQ ID NO:6 were purified with the Ni-NTA system according to the manufacturer's instructions (Qiagen) from 50_ml cultures. Protein concentrations were determined by the Bradford method with bovine serum albumin as the standard (Bio-Rad). The purified proteins were stored at −80° C. Samples were analyzed by SDS-PAGE with the NuPAGE system (Invitrogen). Proteins purified according to this protocol were used for screening of carbonyl-containing compounds and biocatalytic reactions.

Example 1

Detection of RedAm Activity

All the reactions were conducted at 25° C. in 96-microwell plates. Amination reaction: to a reaction mixture (200 μL) containing 10-50 mM carbonyl-containing substrate, 0.5 mM NADH and 0.5 mM NADPH in 225 mM $NH_4Cl/NH_4OH$ buffer (pH 9.8) was added 30 μL of cell-free extract.

Reverse Deamination reaction: to a reaction mixture (200 μL) containing 10-50 mM ketone substrate, 0.5 mM $NAD^+$ and 0.5 mM $NADP^+$ in 100 mM $NaHCO_3/Na_2CO_3$ buffer (pH 9.8) was added 30 μL of cell-free extract. Absorbance at 340 nm was measured immediately and monitored for 4 h. A background plate was established in the same manner but with a mixture lacking the carbonyl-containing substrate (amine in the case of deamination reaction) substrate. An active enzyme corresponds to a well exhibiting a higher slope in the reaction well over the background well.

Substrates which can be used to detect RedAm activity are for instance cyclohexanone, pentan-1-one, pentan-2-one and 2-methylpropanal for the amination reaction, and cyclohexylamine, pentan-1-amine, penta-2-amine and isobutylamine for the reverse deamination reaction.

Example 2

Screening of Carbonyl-Containing Compounds with Ammonia as Amine Source

All the reactions were conducted at 25° C. in spectrophotometric cell (10 mm light path). To a mixture of ammonium formate buffer (2 M $NH_4HCO_2/NH_4OH$, pH 9.5), NADH or NADPH (0.2 mM) and an appropriate amount of purified enzyme was added. Carbonyl-containing compound (5 or 10 mM) is then added to initiate the reaction (reaction final volume 100 μL). The initial slope measured at 340 nm determined the specific activity of the enzyme according to Beer-Lambert's law and the molar absorptivity of β-NADH ($\epsilon = 6298$ $M^{-1}$ $cm^{-1}$).

Results

The table 2A hereunder shows the results (detected activity/non detected activity) of the screening of carbonyl-containing compounds for enzymes of SEQ ID NO:1, SEQ ID NO:2 and SEQ ID NO:3.

TABLE 2A

| carbonyl-containing substrates tested. | | | | |
|---|---|---|---|---|
| Carbonyl-containing compound of formula (I) | Resulting amine of formula (II) | SEQ ID NO: 1 | SEQ ID NO: 2 | SEQ ID NO: 3 |
| levulinic acid | No reaction- not substrate | nd | nd | nd |
| 4-oxo-2-aminopentanoic acid | No reaction- not substrate | nd | nd | nd |
| methyl levulinate | No reaction- not substrate | nd | nd | nd |
| cyclohexanone | cyclohexylamine | d | d | d |
| 2-methylcyclohexanone | 2-methylcyclohexylamine | d | d | d |
| 3-methylcyclohexanone | 3-methylcyclohexylamine | d | d | d |
| 4-methylcyclohexanone | 4-methylcyclohexylamine | d | d | d |
| 2-cyclohexen-1-one | 2-cyclohexen-1-amine | d | d | d |
| cyclopentanone | cyclopentylamine | d | d | d |
| 2-methylcyclopentanone | 2-methylcyclopentylamine | d | d | d |

TABLE 2A-continued carbonyl-containing substrates tested.

| Carbonyl-containing compound of formula (I) | Resulting amine of formula (II) | SEQ ID NO: 1 | SEQ ID NO: 2 | SEQ ID NO: 3 |
|---|---|---|---|---|
| 3-methylcyclopentanone | 3-methylcyclopentanamine | d | d | d |
| pentan-3-one | pentan-3-amine | d | d | d |
| hexan-3-one | hexan-3-amine | d | nd | d |
| pentan-2-one | pentan-2-amine | d | d | d |
| but-3-en-2-one | but-3-en-2-amine | d | nd | nd |
| 3-hydroxybutan-2-one | 3-amino-2-hydroxybutane | d | d | d |
| pentanal | pentan-1-amine | d | d | d |
| 2-methylbutanal | 2-methylbutan-1-amine | d | d | d |
| isobutyraldehyde | isobutylamine | d | d | d |
| 4-hydroxybutan-2-one | 4-amino-1-hydroxybutane | d | d | d |
| benzaldehyde | benzylamine | d | nd | nd |
| 3,5-dimethylcyclohexanone | 3,5-dimethylcyclohexanamine | d | nd | d |
| 1-cyclohexylethanone | 1-cyclohexylethanamine | d | nd | d |

TABLE 2A-continued carbonyl-containing substrates tested.

| Carbonyl-containing compound of formula (I) | Resulting amine of formula (II) | SEQ ID NO: 1 | SEQ ID NO: 2 | SEQ ID NO: 3 |
|---|---|---|---|---|
| 3-methylbutan-2-one | 3-methylbutan-2-amine | d | d | d |
| 2,3-dihydro-1H-inden-1-one | 2,3-dihydro-1H-inden-1-amine | nd | nd | d | d: detected activity, nd: not detected activity.

The following substrates were tested for the enzyme of SEQ ID NO:4. The specific activity for said substrates were also determined:

TABLE 2B

| Carbonyl-containing compound of formula (I) | Resulting amine of formula (II) | Detection of the expected compound | Specific activity (mU.mg$^{-1}$)$^c$ |
|---|---|---|---|
| 4-oxopentanoic acid | No reaction- not substrate | nd | — |
| 2-amino-4-oxopentanoic acid | No reaction- not substrate | nd | — |
| methyl 4-oxopentanoate | No reaction- not substrate | nd | — |
| cyclohexanone | cyclohexanamine | d | 9.82$^a$ |
| pentanal | pentan-1-amine | d | 89.1$^a$ |
| 2-methylbutanal | 2-methylbutan-1-amine | d | 129.6$^a$ |
| 2-methylpropanal | 2-methylpropan-1-amine | d | 51.5$^a$ |

TABLE 2B-continued carbonyl-containing substrates tested for the enzyme of SEQ ID NO: 4.

| Carbonyl-containing compound of formula (I) | Resulting amine of formula (II) | Detection of the expected compound | Specific activity (mU.mg$^{-1}$)$^c$ |
|---|---|---|---|
| benzaldehyde | benzylamine | d | Not determined | d: detected activity, nd: not detected activity.
For the specific activity:
$^a$reaction performed with 0.2 mM NADH
$^c$ the best specific activity obtained with 10 mM of carbonyl-containing compound between reaction with NADPH or NADH is presented here.

The table 3 hereunder shows the specific activities of enzymes of SEQ ID NO:1, SEQ ID NO:2 and SEQ ID NO:3 towards some carbonyl-containing compounds with ammonia as amine source.

TABLE 3 specific activities of the enzymes of SEQ ID NO: 1, SEQ ID NO: 2 and SEQ ID NO: 3 for several carbonyl-containing compounds.

| Carbonyl-containing compound of formula (I) | Resulting amine of formula (II) | Specific activity (mU.mg$^{-1}$)$^c$ | | |
|---|---|---|---|---|
| | | SEQ ID NO: 1 | SEQ ID NO: 2 | SEQ ID NO: 3 |
| cyclohexanone | cyclohexylamine | 196.2$^a$ | 135.9$^a$ | 614.5$^a$ |
| 2-methylcyclohexanone | 2-methylcyclohexylamine | 175.3$^b$ | 14.8$^b$ | 337.0a |
| 3-methylcyclohexanone | 3-methylcyclohexylamine | 160.9$^b$ | 37.0$^b$ | 206.5$^b$ |
| 4-methylcyclohexanone | 4-methylcyclohexylamine | 85.2$^a$ | 20.4$^b$ | 170.1$^b$ |
| 2-methylcyclopentanone | 2-methylcyclopentylamine | 65.2$^b$ | 8.8$^b$ | 90.3$^b$ |
| pentan-3-one | pentan-3-amine | 48.2$^b$ | 3.6$^b$ | 192.0$^b$ |

TABLE 3-continued specific activities of the enzymes of SEQ ID NO: 1, SEQ ID NO: 2 and SEQ ID NO: 3 for several carbonyl-containing compounds.

| Carbonyl-containing compound of formula (I) | Resulting amine of formula (II) | Specific activity (mU.mg$^{-1}$)$^c$ | | |
|---|---|---|---|---|
| | | SEQ ID NO: 1 | SEQ ID NO: 2 | SEQ ID NO: 3 |
| pentan-2-one | pentan-2-amine | 9.0$^b$ | 6.4$^b$ | 51.2$^b$ |
| 3-hydroxybutan-2-one | 3-amino-butan-2-ol | 177.7$^b$ | 42.4$^b$ | 324.4$^b$ |
| pentanal | pentan-1-amine | 26.8$^b$ | 72.9$^b$ | 57.8$^b$ |
| 2-methylbutanal | 2-methylbutan-1-amine | 75.2$^b$ | 231.9$^a$ | 159.4$^a$ |
| isobutyraldehyde | isobutylamine | 556.5$^a$ | 119.2$^a$ | 541.0$^a$ |
| 3,5-dimethylcyclohexanone | 3,5-dimethylcyclohexanamine | 9.7$^b$ | nd | 61.6$^b$ |
| cyclopentanone | cyclopentanamine | 5.6$^b$ | 24.2$^b$ | 60.6$^b$ |
| 3-methylcyclopentanone | 3-methylcyclopentanamine | 7.7$^b$ | 13.9$^b$ | 23.3$^b$ |
| 1-cyclohexylethanone | 1-cyclohexylethanamine | 2.1$^b$ | nd | 64.0$^b$ |
| cyclohex-2-enone | cyclohex-2-enamine | 7.4$^b$ | 2.5$^a$ | 37.1$^b$ |
| indan-1-one | indan-1-amine | nd | nd | 11.9$^b$ |

TABLE 3-continued specific activities of the enzymes of SEQ ID NO: 1, SEQ ID NO: 2 and SEQ ID NO: 3 for several carbonyl-containing compounds.

| Carbonyl-containing compound of formula (I) | Resulting amine of formula (II) | Specific activity (mU·mg⁻¹)[c] | | |
|---|---|---|---|---|
| | | SEQ ID NO: 1 | SEQ ID NO: 2 | SEQ ID NO: 3 |
| (ethyl propyl ketone, O) | (2-aminopentane, NH₂) | 6.8[b] | nd | 28.1[b] |
| (3-methyl-2-butanone, O) | (3-methyl-2-butylamine, NH₂) | 125.8[b] | 68.2[a] | 245.6[b] | nd: not detected activity
[a] reaction performed with 0.2 mM NADH,
[b] reaction performed with 0.2 mM NADPH,
[c] the best specific activity obtained with 10 mM of carbonyl-containing compound between reaction with NADPH or NADH is presented here.

The table 4 hereunder shows the specific activities of enzymes of SEQ ID NO:5 and SEQ ID NO:6 towards some carbonyl-containing compounds with ammonia as amine source.

TABLE 4 specific activities of the enzyme of SEQ ID NO: 5 for several carbonyl-containing compounds with ammonia as amine source.

| Carbonyl-containing compound of formula (I) | Resulting amine of formula (II) | Specific activity (mU·mg⁻¹) | |
|---|---|---|---|
| | | SEQ ID NO: 5[a] | SEQ ID NO: 6[b] |
| (cyclohexanone) | (cyclohexylamine) | 75.6 | 13.9 |
| (2-pentanone) | (2-aminopentane) | 6.1 | nd |
| (2-methylpropanal) | (isobutylamine) | 103.7 | 33.4 | nd: not detected activity.
Reaction performed with a mixture NADH/NADPH (0.1 mM each) and
[a] 5 mM of carbonyl-containing compound
[b] 10 mM of carbonyl-containing compound.

Enzyme of SEQ ID NO:1 SEQ ID NO:2, and SEQ ID NO:3 showed much higher specific activities (196.2, 135.9, 614.5 respectively) towards cyclohexanone than Bbad-AmDH (11.3 mU·mg⁻¹), Cal-AmDH (12.7 mU·mg⁻¹) (as described in Pushpanath et al., supra) and PheDH-AmDH K77S/N276L (27 mU·mg⁻¹). This latter is also less active towards 2-methylcyclohexanone (19.3 mU·mg⁻¹) and 3-methylcyclohexanone (41.1 mU·mg⁻¹) than enzymes of SEQ ID NO:1 (175.3 and 160.9 respectively) and SEQ ID NO:3 (337.0 and 206.5, respectively). Moreover, enzymes of SEQ ID NO:1 and NO:3 show high activities toward 2-methylpropanal (556.5 and 541.0 mU·mg⁻¹ respectively), activity not reported before in the literature.

The enzymes of SEQ ID NO:1, SEQ ID NO:2, SEQ ID NO:3 and SEQ ID NO:4 were also active with respect to cyclic imine substrates. In particular, these enzymes were able to catalyze to reduction of into

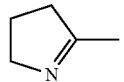

into

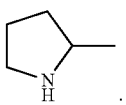

Example 3

Preliminary Results of Screening of Carbonyl-Containing Compounds with Methylamine as Amine Source All the reactions were conducted at 25° C. in spectrophotometric cell (10 mm light path). To a mixture of TRIS.HCl buffer (50 mM, pH 9.5), NADH and NADPH (0.1 mM each), methylamine (500 mM) and an appropriate amount of purified enzyme was added. Carbonyl-containing compound (5 mM) is then added to initiate the reaction (reaction final volume 100 µL). The initial slope measured at 340 nm determined the specific activity of the enzyme according to Beer-Lambert's law and the molar absorptivity of β-NADH ($\epsilon$=6298 M⁻¹ cm⁻¹).

Results

The table 5 hereunder shows the preliminary specific activities of enzymes of SEQ ID NO:1, SEQ ID NO:2, SEQ ID NO:3, SEQ ID NO:4 and SEQ ID NO:5 towards some carbonyl-containing compounds with methylamine as amine source.

TABLE 5 specific activities of the enzymes of SEQ ID NO: 1, SEQ ID NO: 2, SEQ ID NO: 3, SEQ ID NO: 4 and SEQ ID NO: 5 for several carbonyl-containing compounds with methylamine as amine source.

| Carbonyl-containing compound of formula (I) | Resulting amine of formula (II) | Specific activity (mU.mg$^{-1}$)$^a$ | | | | |
|---|---|---|---|---|---|---|
| | | SEQ ID NO: 1 | SEQ ID NO: 2 | SEQ ID NO: 3 | SEQ ID NO: 4 | SEQ ID NO: 5 |
| 2-methylpropanal | N-methyl-2-methylpropylamine | 144.5 | 150.2 | 851.3 | 30.3 | 262.6 |
| cyclohexanone | N-methylcyclohexylamine | 10.1 | nd | 90.4 | nd | 12.6 | nd: not detected activity.
$^a$reaction performed with a mixture NADH/NADPH (0.1 mM each).

The enzymes of SEQ ID NO:1, SEQ ID NO:3 and SEQ ID NO:5 were active on both substrates 2-methylpropanal and cyclohexanone with methylamine, enzyme of SEQ ID NO:3 showing the highest specific activities (851.3 and 90.4 mU/mg of purified enzyme for 2-methylpropanal and cyclohexanone respectively). These preliminary results showed that enzymes of SEQ ID NO:2 and SEQ ID NO:4 are active on 2-methylpropanal.

Example 4

UHPLC-UV-MS Analyses of Reaction of 2-Methylcyclohexanone, Pentanal and Pentan-2-One with the Enzymes of SEQ ID NO:1 and SEQ ID NO:2 and Ammonia as Amine Source To confirm the formation of the amine, some reactions have been carried out on 9 μmol scale with NADPH recycling system and the reaction mixture analyzed by UHPLC-UV-MS after derivatization with benzoyl chloride. The resulting analyzes were compared to analyzes obtained with the commercial amines corresponding to the expected products, derivatized according to the same procedure.

Reaction conditions: To a reaction mixture containing 30 mM of carbonyl-containing compound, 0.4 mM NADPH, 31 mM glucose, 3 U/ml GDH in 2M ammonium formate buffer pH 9.0 was added 0.5 mg/ml of purified enzyme. The reaction was shaken at 400 rpm for 48h at 30° C. Reaction monitoring:

The reaction mixture was monitored by UHPLC UV/MS after derivatization with benzoyl chloride (BzCl).

Procedure for BzCl derivatization: To 20 μL of reaction mixture were added 10 μL of a 1 M Na$_2$CO$_3$/NaHCO$_3$ aqueous solution, 40 μL of H$_2$O, and 30 uL of a 50 mM BzCl solution in acetonitrile. The mixture was vortexed for 30s and then quenched by the addition of 20 μl of a 1 M HCl aqueous solution and 30 μl of a 1/1 solution of H$_2$O/acetonitrile. After centrifugation (10 krpm, 10 min, ambient temperature) and filtration (0.22 μm), the mixture was analyzed by UHPLC (F5 Kinetex column; solvent A acetonitrile, solvent B H$_2$O+0.1% HCO$_2$H; flow 0.5 ml/min; injection volume 3 μL; UV detection 250 nm and mass detection (ESI positive mode, 75 V); column temperature 25° C.; gradient mode: A/B 20/80 (1 min) to 70/30 in 3 min (2 min) followed by reequilibration time.

The tested carbonyl-containing compounds were racemic 2-methylcyclohexanone, pentanal and pentan-2-one. The commercial amines, used as references, were racemic 2-methylcyclohexylamine, pentan-1-amine and racemic pentan-2-amine.

Figure 2:
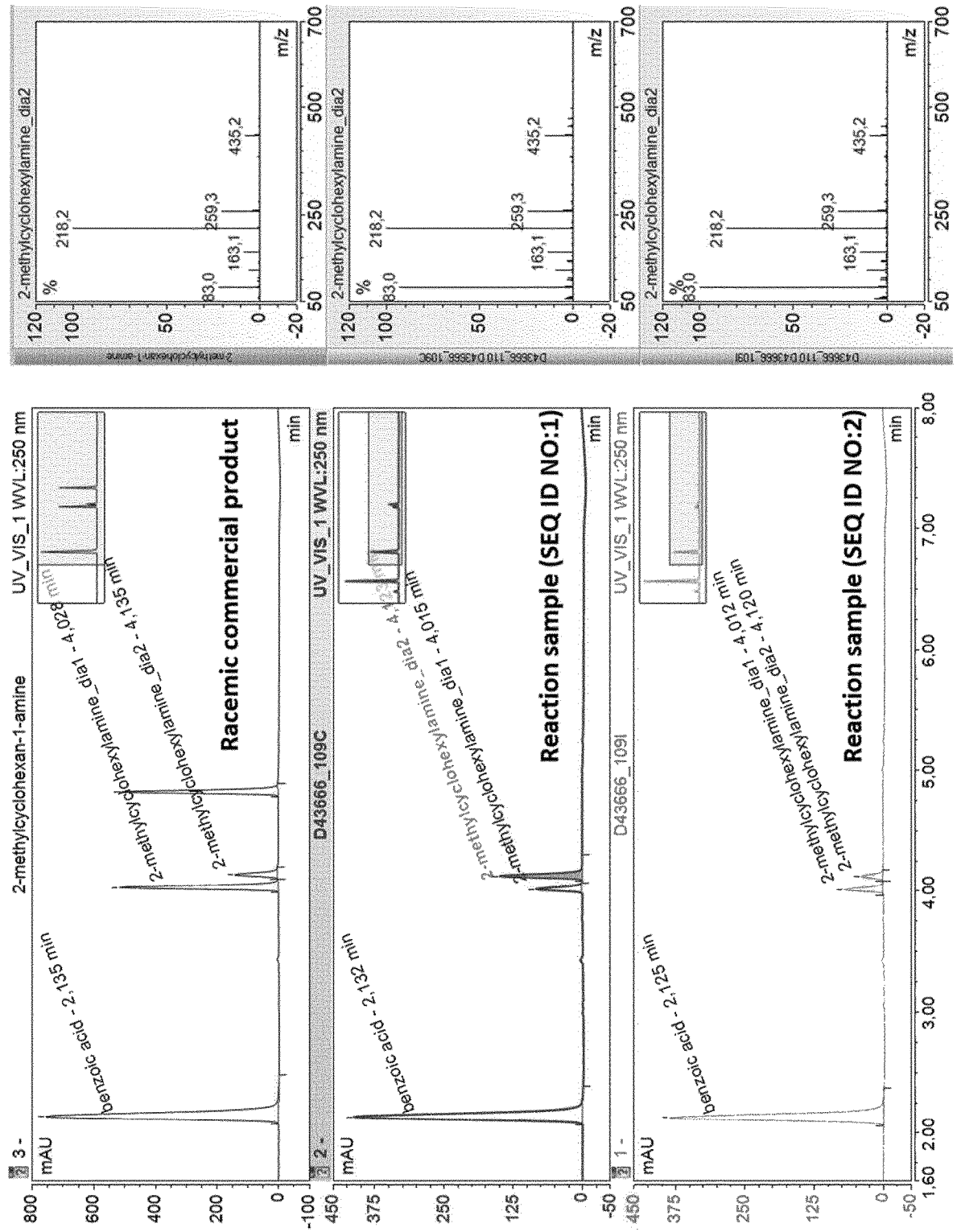
FIG. 2 shows the UHPLC-UV-MS chromatogram of racemic commercial 2-methylcyclohexylamine and that of reaction sample corresponding to the reaction of 2-methylcyclohexanone with enzyme of SEQ ID NO:1 or SEQ ID NO:2 after derivatization with benzoyl chloride. MS conditions: electrospray ionization, positive mode; theoretical mass [M+H] =218.2; [M+MeCN+H]=259.2; [2M+H]= 435.3.
Figure 3:
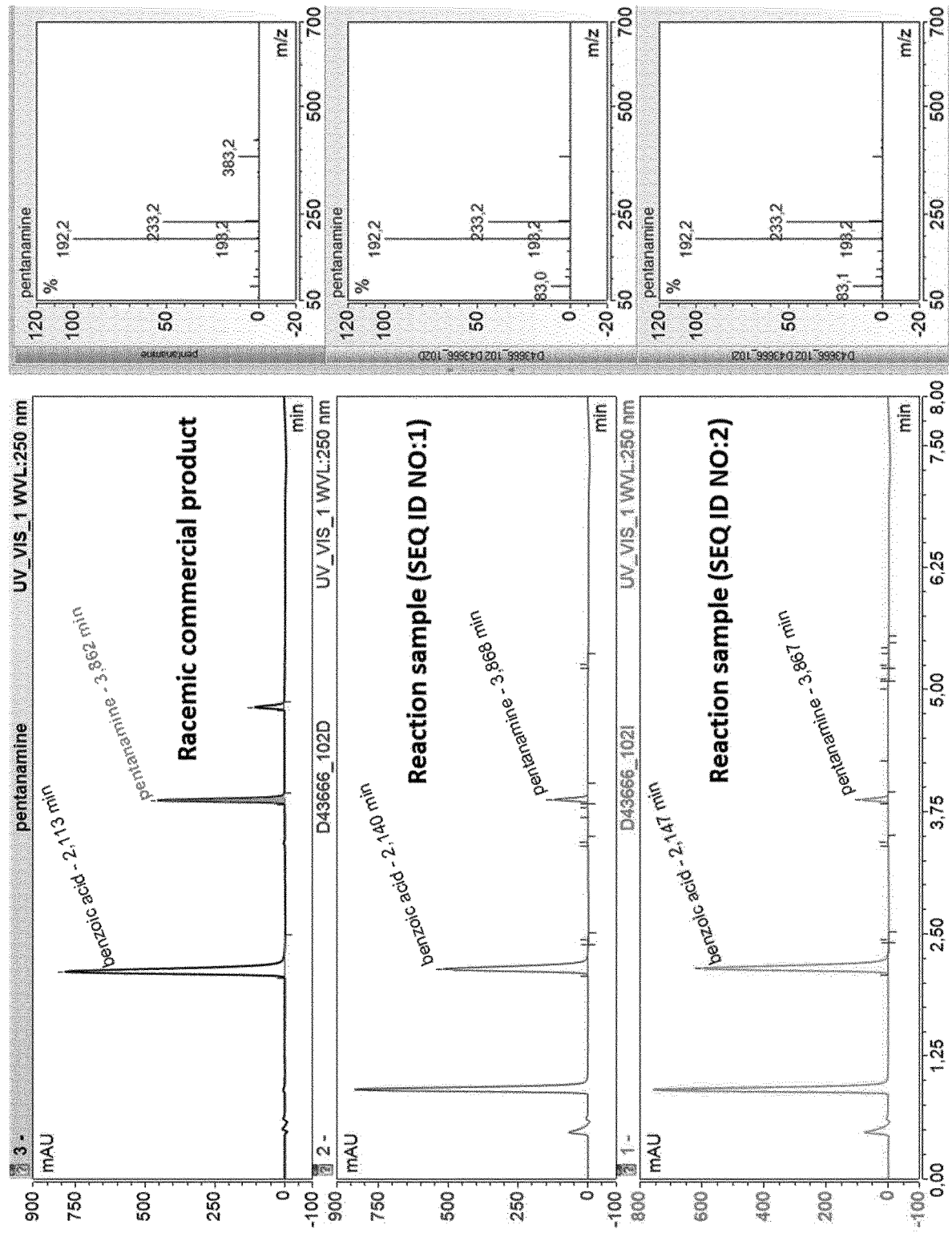
FIG. 3 shows the UHPLC-UV-MS chromatogram of commercial pentan-1-amine and that of the reaction sample corresponding to the reaction of pentanal with the enzyme of SEQ ID NO:1 or SEQ ID NO:2 after derivatization with benzoyl chloride. MS conditions: electrospray ionization, positive mode; theoretical mass [M+H]=192.2; [M+MeCN+H]=233.2; [2M+H]=383.2.
Figure 4:
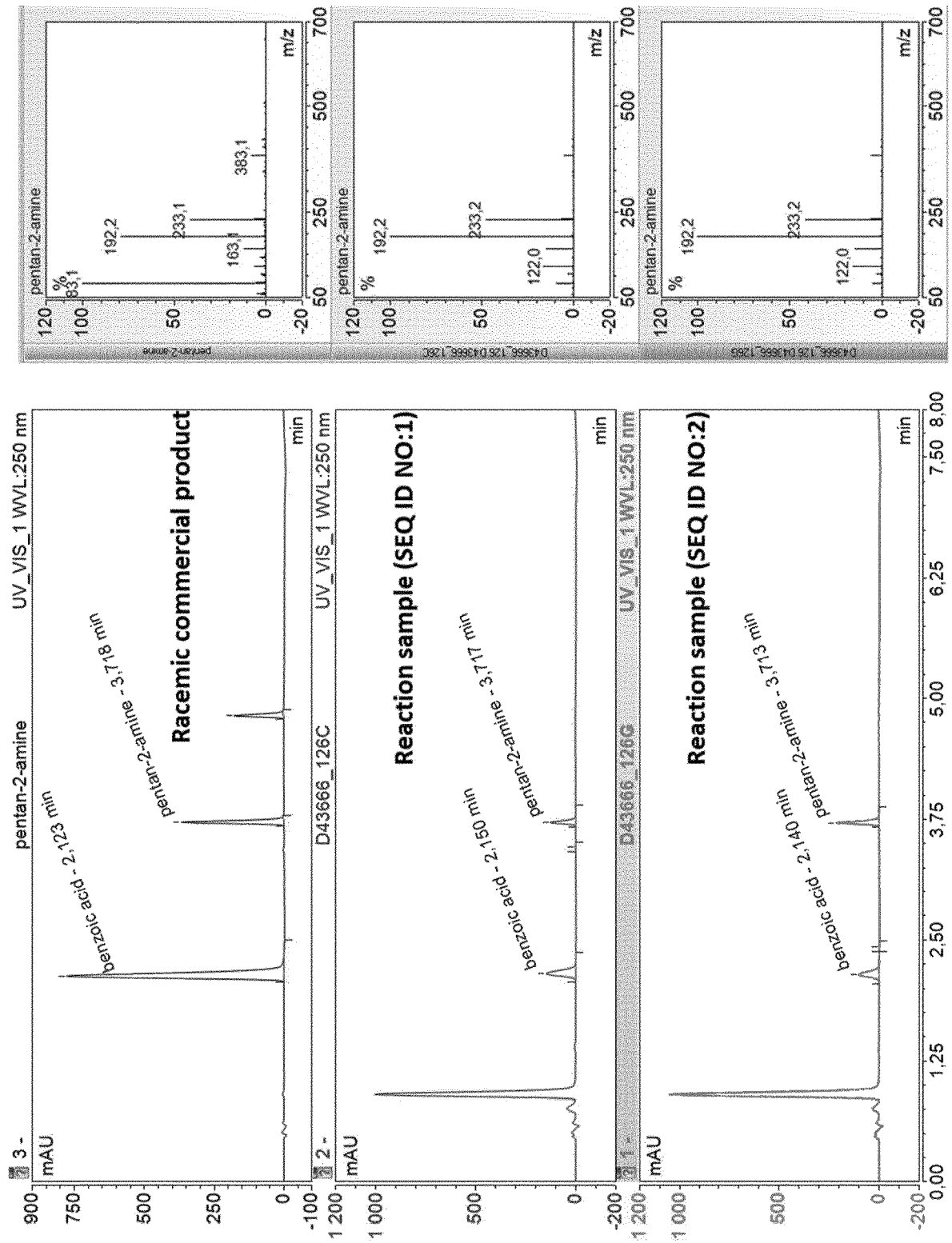
FIG. 4 shows UHPLC-UV-MS chromatogram of racemic commercial pentan-2-amine and that of the reaction sample corresponding to the reaction of pentan-2-one with the enzyme of SEQ ID NO:1 or SEQ ID NO:2 after derivatization with benzoyl chloride.

Results:

UHPLC chromatograms with UV detection and MS spectrum of the resulting derivatized amines are presented in FIGS. 2, 3 and 4. These chromatograms show that the expected amines were actually formed for each enzyme of SEQ ID NO:1 and SEQ ID NO:2: elution peaks with a retention time and a mass spectrum corresponding to the commercial amine were detected in each case. In the case of reaction with 2-methylcyclohexanone, enzyme of SEQ ID NO:1 preferentially formed the diastereoisomer labelled "dia 2" on the chromatogram whereas diastereoisomer labelled "dia 1" is preferentially formed with enzyme of SEQ ID NO:2 (FIG. 2).

Example 5

Determination of the Configuration of the Amine Product Resulting from the Reductive Amination of Pentan-2-One, 2-Methyl-Cyclohexanone and 3-Methyl-Cyclohexanone with the Enzymes of SEQ ID NO:1 and SEQ ID NO:2 and Ammonia as Amine Source In order to determine the configuration of the resulting amines, some reactions have been carried out on 9 μmol scale to enable extraction of enough material for analysis. The configuration has been determined by comparison with bibliographic data and injection of commercial racemic amines.

Reaction conditions:

To a reaction mixture containing 30 mM of carbonyl-containing compound, 0.4 mM NADPH, 31 mM glucose, 3 U/ml GDH in 2M ammonium formate buffer pH 9.0 was added 0.5 mg/ml of purified enzyme. The reaction was shaken at 400 rpm for 48 h at 30° C. 2-methyl-cyclohexanone and 3-methyl-cyclohexanone were used in racemic form.

Reaction Monitoring:

The reaction mixture was analyzed by UHPLC-UV after derivatization with (S)-2-(5-fluoro-2,4-dinitrophenylamino)propanamide (FDAA) or chiral GC-FID after derivatization with trifluoroacetic acid anhydride (TFAA) or acetic anhydride for enantiomeric/diastereoisomeric ratio determination.

Procedure for the derivatization with (S)-2-(5-fluoro-2,4-dinitrophenylamino)propanamide (FDAA). To 20 μL of a 10 mM reaction mixture were added 8 μL of a 1 M NaHCO$_3$ aqueous solution and 20 μL of a 4 mg·ml FDAA solution in acetone. The mixture was stirred (400 rpm) at 50° C. for 1 h and then quenched by the addition of 4 μL of 2 M HCl aqueous solution and centrifuged (10 min, 10 000 rpm) to remove proteins. The resulting supernatant (25 μL) was diluted in MeCN (75 μL), filtered (0.22 μm), and analyzed by UHPLC-UV at 340 nm.

Procedures for Chiral GC Analyzes:

For reaction with pentan-2-one: 30 μL of a solution of KOH 10 N and 400 μL of dichloromethane were added to 150 μL of the reaction mixture and the organic phase (350 μL) was taken, dried over MgSO$_4$. 300 uL of the resulting dried solution was derivatized with 20 uL of acetic anhydride solution (50 mg DMAP/ml of acetic anhydride) 30 min at room temperature. After addition of 150 μL of water and 30 min stirring at room temperature, the organic phase was dried (MgSO$_4$) and analyzed by GC-FID (Chiracel Dex-CB GC column) to determine the enantiomeric ratio according to retention times of enantiomers reported by Knaus et al. (Green Chem., 2017, 19, 453).

For reaction with 2- and 3-methylcyclohexanone: 30 μL of a solution of KOH (10 N and 300 μL of ethyl acetate were added to 150 μL of the reaction mixture and the organic phase (270 μL) was taken, dried over MgSO$_4$. The resulting dried solution was derivatized with 20 μL of pure trifluoroacetic anhydride 30 min at 30° C. After addition of 300 μL of a saturated solution of NaHCO$_3$ and 30 min stirring at room temperature, the organic phase was dried (MgSO4) and analyzed by GC-FID (Chiracel Dex-CB GC column) to determine the diastereoisomeric ratio according to retention times of enantiomers reported by Richter et al. (Org. Biomol. Chem., 2015, 13, 8843).

Results

GC-FID chromatograms of the derivatized extracted reaction mixture are presented in FIGS. 5, 6 and 7 together with the chromatograms of derivatized commercial amines.

After analyzes of the reaction mixtures according to the described procedures, the results were as follows:

For reaction with pentan-2-one, the enantiomeric excess of (S)-pentan-2-amine was >97% for enzymes of SEQ ID NO:1 and NO:2 (FIG. 5).

For reaction with racemic 2-methylcyclohexanone, the diastereoisomeric excess of (1S)-2-methylcyclohexanamine was 91% and 69% for enzyme of SEQ ID NO:1 and SEQ ID NO:2 respectively. Diastereoisomer (1S, 2R) is preferentially formed with enzyme of SEQ ID NO:1 and diastereoisomer (1S, 2S) with enzyme of SEQ ID NO:2 (FIG. 6).

For reaction with racemic 3-methylcyclohexanone, the diastereoisomeric excess of (1S)-3-methylcyclohexanamine was >97% and 95% for enzyme of SEQ ID NO:1 and SEQ ID NO:2 respectively). The major diastereoisomer formed with both enzymes is (1S, 3R)-3-methylcyclohexylamine (FIG. 7).

Example 6

Semi-Preparative-Scale Reductive Amination of Pentan-2-One, 2-Methyl-Cyclohexanone and 3-Methyl-Cyclohexanone with the Enzymes of SEQ ID NO:1 or SEQ ID NO:2 and Ammonia as Amine Source To confirm the formation of the amine, additional reactions were carried out on 1 mmol scale with NADPH recycling system and the products were isolated and analyzed.

Reactions Conditions:

To a reaction mixture (20 mL) containing 50 mM of carbonyl-containing compound, 0.2 mM NADP+, 60 mM D-glucose, 60 U of GDH in 1-2 M ammonium formate buffer (pH 9 or 10.5) purified enzyme of interest (0.1 to 0.5 mg/mL depending on the couple substrate/enzyme) was added. Reactions were stirred at 30° C., at 400 rpm for 6 to 24 h and then basified to pH 12 with 10 M NaOH solution. The products were extracted with diethyl ether (3×20 mL), the combined organic layers were dried (MgSO4) and concentrated to approximately 10 mL before addition of 1.2 eq of a solution of 2 M HCl in diethylether. In case of precipitation, the resulting solid was filtered, washed with cold diethyl ether and dried to afford the desired amine as monohydrochloride salt. Otherwise, 10 mL of distilled water were added and the product extracted with 2×20 mL of water. The combined aqueous phases were washed with diethylether (3×10 mL) to remove the unreacted ketone. The water phase was then lyophilized to afford the desired product as monohydrochloride salt.

Configuration Determination of the Resulting Amines GC-FID Analysis:

40 uL sample of the reaction mixture were withdrawn just before quenching the reaction and monitored by UHPLC-UV. The reaction mixture was derivatized with trifluoroacetic acid anhydride (TFAA) or acetic anhydride and analyzed by chiral GC-FID.

Chiral GC Analyzes:

For reaction with pentan-2-one: 15 μL of a solution of KOH 10 N and 400 μL of dichloromethane were added to 40 μL of the reaction mixture and the organic phase (350 μL) was taken, dried over MgSO$_4$. 300 uL of the resulting dried solution was derivatized with 20 uL of acetic anhydride solution (50 mg DMAP/ml of acetic anhydride) 30 min at room temperature. After addition of 150 μL of water and 30 min stirring at room temperature, the organic phase was dried (MgSO$_4$) and analyzed by GC-FID (Chiracel Dex-CB GC column) to determine the enantiomeric ratio according to retention times of enantiomers reported by Knaus et al. (Green Chem., 2017, 19, 453).

For reaction with 2- and 3-methylcyclohexanone: 15 μL of a solution of KOH (10 N and 300 μL of ethyl acetate were added to 40 μL of the reaction mixture and the organic phase (270 μL) was taken, dried over MgSO$_4$. The resulting dried solution was derivatized with 20 μL of pure trifluoroacetic anhydride 1 h at 30° C. After addition of 300 μL of a saturated solution of NaHCO$_3$ and 30 min stirring at room temperature, the organic phase was dried (MgSO4) and analyzed by GC-FID (Chiracel Dex-CB GC column) to determine the diastereoisomeric ratio and diastereosiomeric excess according to retention times of enantiomers reported by Richter et al. (Org. Biomol. Chem., 2015, 13, 8843) and comparison of $^1$H NMR to the one reported for the cis-3-methylcyclohexylamine hydrochloride salt by Zhou and List. (JACS., 2007, 129, 7498).

Results:

The large-scale reactions confirmed the formation of the expected amines. Indeed, the HPLC chromatograms with UV detection of the resulting isolated amines showed that the expected amines were actually formed for each enzyme of SEQ ID NO:1 and SEQ ID NO:2 since elution peaks with a retention time corresponding to the commercial amine were detected in each case. $^1$H and $^{13}$C NMR spectra of isolated amines confirmed their expected structures. GC-FID chromatograms of the derivatized extracted reaction mixture also confirmed the configuration of the expected amines which were obtained with a high diastereoisomeric or enantiomeric excess, for each enzyme. The results are summarized hereunder:

Resulting amines, yield (isolated mass), Total turnover (TTN) and space time yield (STY):

| substrate | Amine product | Biocatalyst (enzyme loading) | Conversion | Yield (isolated mass) | TTN | STY (g L$^{-1}$ d$^{-1}$) |
|---|---|---|---|---|---|---|
| Pentan-2-one | (S)-pentan-2-amine Obtained as white solid | SEQ ID NO: 2 (0.5 mg/mL) | 57% | 39% (48 mg) | 3016 | 2.4 |
| 2-methylcyclohexanone | (1S, 2R)-2-methylcyclohexylamine Obtained as monochloride salt, white solid | SEQ ID NO: 1 (0.3 mg/mL) | 55% | 35% (52 mg) | 6847 | 2.60 |
| 3-methylcyclohexanone | (1S, 3R)-3-methylcyclohexylamine monochloride salt, yellowish oil | SEQ ID NO: 1 (0.3 mg/mL) | 45% | 40% (60 mg) | 5933 | 2.99 |

Chiral GC-FID Analyses:

(1S, 2R)-2-methylcyclohexylamine hydrochloride was obtained as a mixture of cis/trans product (ratio 90/10) with ed ≥99%.

(1S, 3R)-3-methylcyclohexylamine hydrochloride was obtained as a mixture of cis/trans product (ratio 97/3) with ed ≥99%.

(2S)-pentan-2-amine was obtained with ee ≥97%.

Example 7

UHPLC-UV Analyses of Reaction of 2-Methylpropanal with the Enzyme of SEQ ID NO:3 and Methylamine as Amine Source To confirm the reactivity with methylamine as amine source, a reaction was carried out on 2-methylpropanal with enzyme of SEQ ID NO:3 with methylamine as amine source, the mixture analyzed after derivatization with benzoyl chloride and the product was isolated and analyzed.

Reactions Conditions:

To a reaction mixture (20 mL) containing 50 mM of 2-methylpropanal, 0.2 mM NADP+, 60 mM D-glucose, 60 U of GDH in 50 mM sodium phosphate buffer pH 8 and 75 mM methylamine was added purified enzyme of SEQ ID NO:3 (0.1 mg/mL). The reactions was stirred at 30° C. 400 rpm for 10 h, the reaction was basified to pH 12 with 10 NaOH solution and the product extracted with diethylether (3×20 mL). The combined organic layers were dried (MgSO$_4$) and concentrated under reduced pressure to approximately 10 mL before addition of a solution of 2 M HCl in diethylether (1 mL, 2 mmol). 10 mL of distilled water was added and the product extracted with 2×20 mL of water. The combined aqueous phases were washed with diethylether (3×10 mL) to remove the unreacted aldehyde and then lyophilized.

Result:

N-methylisobutylamine (69 mg, 56% yield, yellowish oil) was obtained as monohydrochloride salt. The formation of N-methylisobutylamine was confirmed by UHPLC analysis with UV detection of the final product. The chromatogram showed elution peaks with retention time corresponding to those of the commercial product. $^1$H and $^{13}$C NMR spectra of the isolated amine confirmed its expected structure.

---

The invention claimed is:

1. A method for the reductive amination of a carbonyl-containing compound selected from aldehydes and ketones devoid of any carboxyl group at position gamma of the carbonyl group comprising contacting a carbonyl-containing compound selected from aldehydes and ketones devoid of any carboxyl group at position gamma of the carbonyl group with an enzyme having reductive aminase (RedAm) activity and comprising an amino acid sequence having at least 90% sequence identity with the amino acid sequence of SEQ ID NO:3, as a catalyst, to reductively aminate said carbonyl-containing compound to an amine-containing compound.

2. The method of claim 1, wherein the carbonyl-containing compound is of formula (I)

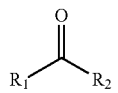

(I)

wherein $R_1$ and $R_2$ are independently selected from H, alkyl, heteroalkyl, alkenyl, aryl, heteroaryl, arylalkyl, heteroaryl alkyl, aryl alkenyl, heteroaryl alkenyl, alkyloxy alkyl, heteroaryloxy alkyl, aryloxy alkyl, and alkanoyl alkyl, said groups being optionally substituted, with proviso that $R_1$ and $R_2$ are not both H, or $R_1$ and $R_2$ form together a saturated or non-saturated ring optionally substituted and/or optionally fused with another ring, wherein the carbonyl-containing group is devoid of any carboxyl group at position gamma of the carbonyl, and wherein the method comprises the step of contacting the carbonyl-containing compound of formula (I) with the enzyme having a reductive aminase (RedAm) activity in the presence of a nitrogen source, and in the presence of a cofactor selected from NADH, NADPH, synthetic analogs thereof and combinations thereof.

3. The method according to claim 2, wherein:
the resulting amine is of formula (II),

wherein $R_1$ and $R_2$ are independently selected from H, alkyl, heteroalkyl, alkenyl, aryl, heteroaryl, arylalkyl, heteroaryl alkyl, aryl alkenyl, heteroaryl alkenyl, alkyloxy alkyl, heteroaryloxy alkyl, aryloxy alkyl, and alkanoyl alkyl, said groups being optionally substituted, with proviso that $R_1$ and $R_2$ are not both H, or
$R_1$ and $R_2$ form together a saturated or non-saturated ring optionally substituted and/or optionally fused with another ring and
$R_3$ is selected from H, alkyl, alkenyl, alkynyl, and aryl, said groups being optionally substituted, and
the nitrogen source provided is $R_3NH_2$ or a salt thereof, wherein $R_3$ is selected from H, alkyl, alkenyl, alkynyl, and aryl, said groups being optionally substituted.

4. The method according to claim 3, wherein $R_3$ is H and the source of nitrogen is ammonia or an ammonium salt.

5. The method according to claim 3, wherein the resulting amine of formula (II) is chiral and obtained in enantiomeric excess.

6. The method according to claim 2, wherein the carbonyl-containing compound has a molecular weight lower than 800 g·mol$^{-1}$.

7. The method according to claim 2, wherein the carbonyl-containing compound is of formula (I):

wherein
$R_1$ and $R_2$ are independently selected from the group consisting of H, $C_1$-$C_{10}$ alkyl, $C_1$-$C_{10}$ heteroalkyl $C_2$-$C_{10}$ alkenyl, $C_6$-$C_{12}$ aryl, $C_4$-$C_{12}$ heteroaryl, $C_6$-$C_{14}$ heteroaryl alkyl, $C_7$-$C_{14}$ arylalkyl, $C_8$-$C_{14}$ aryl alkenyl, $C_2$-$C_{10}$ alkyloxy alkyl, $C_7$-$C_{14}$ aryloxy alkyl, $C_5$-$C_{14}$ heteroaryloxy alkyl and $C_2$-$C_{10}$ alkanoyl alkyl, said groups being optionally substituted by one or several substituents selected from OH, $NH_2$, SH, $NO_2$, —CN, halogen, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, —COX, —C(X)$_3$ with X is a halogen, $CONH_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl, with proviso that $R_1$ and $R_2$ are not simultaneously H, or
$R_1$ and $R_2$ form together a saturated or unsaturated 4-7-member ring optionally substituted and optionally fused to another 4-7-member ring, the one or several optional substituent(s) being selected from OH, $NH_2$, SH, $NO_2$, —CN, halogen, oxo group, $C_1$-$C_6$ alkyl, $C_1$-$C_6$ alkoxy, $C_1$-$C_6$ hydroxyalkyl, $C_1$-$C_6$ halogenoalkyl, $C_1$-$C_6$ aminoalkyl, —COX, —C(X)$_3$ with X is a halogen, —CONH$_2$, —COOH, —C(=O)—R, —NHC(=O)R, —C(=O)NHR, —SC(=O)R, —C(=O)SR, —OC(=O)R, and —C(=O)OR, wherein R is a $C_1$-$C_6$ alkyl.

8. The method according to claim 7, wherein:
$R_1$ and $R_2$ are independently selected from the group consisting of H, $C_1$-$C_{10}$ alkyl, $C_2$-$C_{10}$ alkenyl, $C_6$-$C_{12}$ aryl, $C_7$-$C_{14}$ arylalkyl, and $C_8$-$C_{14}$ arylalkenyl, said groups being optionally substituted by one or several substituents selected from OH, $NH_2$, SH, $NO_2$, —CN, halogen, $C_1$-$C_4$ alkyl, $C_1$-$C_4$ alkoxy, $C_1$-$C_4$ hydroxyalkyl, $C_1$-$C_4$ halogenoalkyl, $C_1$-$C_4$ aminoalkyl, and —C(X)$_3$ with X is a halogen, with proviso that $R_1$ and $R_2$ are not simultaneously H, or
$R_1$ and $R_2$ forms together a ring such that the carbonyl-containing compound is of formula (Ia):

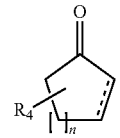

wherein n is an integer selected from 0, 1 or 2, ≈≈≈ means a double or a sound, and $R_4$ is a substituent selected from H, $C_1$-$C_4$ alkyl, an oxo group, —OH, $NH_2$, SH, $NO_2$, —CN, halogen, $C_1$-$C_4$ alkoxy, $C_1$-$C_4$ hydroxyalkyl, $C_1$-$C_4$ halogenoalkyl, $C_1$-$C_4$ aminoalkyl, and —C(X)$_3$ with X a halogen.

9. The method according to claim 7, wherein:
$R_1$ and $R_2$ are independently selected from H, phenyl, $C_1$-$C_4$, alkyl and $C_1$-$C_4$, alkenyl, said groups being optionally substituted by a substituent selected from OH and $C_1$-$C_3$ alkyl, with proviso that $R_1$ and $R_2$ are not simultaneously H, or
$R_1$ and $R_2$ forms together a ring such that the carbonyl-containing compound is of formula (Ia):

wherein n is 1 or 2, ≈≈≈ means a double or a single bound, and $R_4$ is H or a $C_1$-$C_3$ alkyl.

10. The method according to claim 2, wherein the enzyme having a reductive aminase activity is a wild-type enzyme or a variant of a wild-type enzyme, said wild-type enzyme being identified from a bacteria belonging to a genus selected from *Mycobacterium, Cystobacter, Microbacterium*, and *Aminomonas*.

11. The method according to claim 2, wherein the enzyme having a RedAm activity is provided as a purified or a semi-purified enzyme, an enzyme immobilized on a solid support, or is produced in situ by a wild-type cell or a host cell capable of producing said enzyme.

12. The method according to claim 2, said method comprising at least one of the following steps:
- a step of providing the carbonyl compound of formula (I) by oxidation of an alcohol prior to the step of contacting said carbonyl-containing compound of formula (I) with the enzyme having a reductive aminase (RedAm) activity,
- a step of recovering the amine of formula (II), and/or
- a step of purifying the amine of formula (II).

13. The method according to claim 1, wherein the enzyme comprises the amino acid sequence of SEQ ID NO:3.

14. The method according to claim 2, wherein the enzyme comprises the amino acid sequence of SEQ ID NO:3.

15. The method according to claim 2, wherein the enzyme comprises an amino acid sequence having at least 93% sequence identity with the amino acid sequence of SEQ ID NO:3.

16. The method according to claim 2, wherein the enzyme comprises an amino acid sequence having at least 95% sequence identity with the amino acid sequence of SEQ ID NO:3.

17. The method according to claim 2, wherein the enzyme comprises an amino acid sequence having at least 97% sequence identity with the amino acid sequence of SEQ ID NO:3.

18. The method according to claim 2, wherein the enzyme comprises an amino acid sequence having at least 99% sequence identity with the amino acid sequence of SEQ ID NO:3.

\* \* \* \* \*

UNITED STATES PATENT AND TRADEMARK OFFICE
CERTIFICATE OF CORRECTION

PATENT NO. : 11,118,200 B2
APPLICATION NO. : 16/628688
DATED : September 14, 2021
INVENTOR(S) : Carine Vergne-Vaxelaire, Véronique De Berardinis and Anne Zaparucha Page 1 of 1

It is certified that error appears in the above-identified patent and that said Letters Patent is hereby corrected as shown below:

In the Specification

Column 4,
Line 37, "C aminoalkyl," should read --$C_1$-$C_6$ aminoalkyl,--.
Line 47, "NH2, SH," should read --$NH_2$, SH,--.

Column 5,
Line 45, "formula (II)(II)," should read --formula (II)--.

Column 18,
Line 48, "(His6)," should read --$(His_6)$,--.

Column 28,
Line 66, "to 500 M," should read --to 500 µM,--.

Column 49,
Line 20, "areaction" should read --$^a$ reaction--.

In the Claims

Column 76,
Line 31, "a sound," should read --a single bound--.

Column 77,
Line 1, "to claim 2," should read --to claim 3,--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 12

<210> SEQ ID NO 1
<211> LENGTH: 335
<212> TYPE: PRT
<213> ORGANISM: Mycobacterium smegmatis

<400> SEQUENCE: 1

Met Ser Asp Ile Arg Ala Val Val Tyr Gly Val Gly Ala Met Asn Ser
1               5                   10                  15

Ile Val Ala Gly Met Leu Leu Asp Lys Gly Val Gln Ile Val Gly Ala
            20                  25                  30

Ile Ala Arg Ser Pro Gln Lys Val Gly Gln Asp Leu Gly Asp Leu Leu
        35                  40                  45

Gly Leu Gly Arg Gln Leu Gly Val Ala Val Ser Asp Asp Ala Ala Glu
    50                  55                  60

Val Leu Glu Gln Thr His Pro Asp Ile Ala Val Ile Ala Val Asn Ser
65                  70                  75                  80

Tyr Leu Thr Asp Ala Val Glu Gln Leu Arg Ile Cys Ala Glu His Gly
                85                  90                  95
```

-continued

```
Val Asn Ala Val Thr Leu Ser Glu Glu Met Leu Tyr Pro Trp Glu Thr
                100                 105                 110

Ser Pro Glu Leu Ser Ala Glu Leu Asp Ala Leu Ala Lys Ser Thr Gly
            115                 120                 125

Ala Thr Leu Thr Gly Thr Gly Tyr Gln Asp Thr Phe Trp Val Asn Met
        130                 135                 140

Ile Ala Leu Leu Met Gly Thr Ala His Arg Ile Asp Thr Val Arg Gly
145                 150                 155                 160

Lys Ala Ser Trp Asn Val Asp Asp Phe Gly Pro Glu Leu Ala Thr Ala
                165                 170                 175

Gln Gln Val Gly Arg Thr Val Ala Glu Phe Asp Glu Trp Val Arg Gly
            180                 185                 190

Ala Gln Arg Pro Pro Thr Phe Gly Arg Asn Val Leu Asp Ala Leu Val
        195                 200                 205

Ala Asp Thr Gly Leu Thr Val Lys Ser Ile Thr Thr Ala Thr Arg Pro
210                 215                 220

Asp Ile Ala Ser Ala Ala Met Arg Ser Glu Ala Leu Gly Ile Asp Leu
225                 230                 235                 240

Ala Pro Gly Asp Val Ile Gly Phe Thr Asp Ile Asp Arg Ile Glu Thr
                245                 250                 255

Glu Glu Gly Pro Val Phe Glu Phe Glu Met Ser Gly Arg Val Tyr Gly
            260                 265                 270

Pro Gly Glu Gly Asp Ile Asn Glu Trp Thr Ile Glu Gly Glu Pro Asn
        275                 280                 285

Leu Phe Leu Ser Asn Gly Thr Val Pro Thr Gln Thr Thr Thr Cys Thr
290                 295                 300

Gln Met Val Asn Arg Ile Pro Asp Val Ile Ala Ala Pro Pro Gly Ile
305                 310                 315                 320

Val Thr Val Asp Arg Leu Pro Arg Leu Arg Tyr Arg Pro Gln Phe
                325                 330                 335

<210> SEQ ID NO 2
<211> LENGTH: 342
<212> TYPE: PRT
<213> ORGANISM: Cystobacter fuscus DSM 2262

<400> SEQUENCE: 2

Met Ser Lys Arg Pro Ile Arg Ile Ile Gln Trp Gly Cys Gly Leu Met
1               5                   10                  15

Gly Gln Thr Leu Ile Arg Thr Leu Arg Glu Lys Gly Ala Glu Leu Val
            20                  25                  30

Gly Ala Ile Asp His Asn Ala Ala Arg Arg Asp Arg Asp Ala Gly Glu
        35                  40                  45

Val Ala Gly Leu Gly Gln Ser Leu Gly Val Arg Ile His Pro Pro Asp
    50                  55                  60

Gln Ala Asp Ala Val Phe Arg Glu Ala Arg Ala Asp Val Cys Ile Leu
65                  70                  75                  80

Cys Thr Arg Ser Ile Met Ser Glu Leu Ala Gly Ala Leu Arg Val Ala
                85                  90                  95

Ala Arg His Gly Val Asn Ala Ile Thr Ile Gly Glu Glu Ala Phe Tyr
            100                 105                 110

Pro Trp Thr Thr Ser Gln Ala Leu Thr Glu Glu Leu Asp Gln Leu Ala
        115                 120                 125

Arg Ala Asn Asp Cys Thr Leu Thr Gly Ser Gly Phe Gln Asp Val Phe
    130                 135                 140
```

```
Trp Gly Asn Leu Ile Thr Val Leu Ala Gly Ala Thr His Arg Ile Asp
145                 150                 155                 160

Arg Ile Val Gly Leu Thr Gln Tyr Asn Ala Asp Tyr Gly Ser Ala
            165                 170                 175

Leu Ala Gln Lys His Gly Val Gly Leu Asp Pro Glu Thr Phe Ala Ala
            180                 185                 190

Arg Ile Gly Ala Ser Asn Ser Pro Ser Tyr Val Trp Asn Ser Asn Glu
            195                 200                 205

Trp Leu Cys Ala Gln Leu Gly Trp Arg Val Arg Asp Ile Arg Gln Gln
210                 215                 220

Leu Leu Pro Thr Thr His Thr Gly Thr Leu Arg Ser Ala Ser Leu Gly
225                 230                 235                 240

Arg Glu Val Pro Ala Gly His Ala Thr Gly Met Lys Ala Val Val Val
                245                 250                 255

Thr Glu Thr His Glu Gly Pro Val Ile Glu Thr His Cys Val Gly Lys
                260                 265                 270

Leu Tyr Ala Pro Gly Glu Val Asp Leu Asn Glu Trp Thr Leu Arg Gly
            275                 280                 285

Glu Pro Asp Thr Thr Val Thr Ile Arg Gln Pro Ala Thr Pro Ala Leu
290                 295                 300

Thr Cys Ala Thr Val Leu Asn Arg Leu Pro Gln Leu Leu Ala Ala Pro
305                 310                 315                 320

Pro Gly Phe Val Thr Thr Asp Arg Phe Thr Pro Ala Thr Tyr Val Ser
            325                 330                 335

Arg Leu Glu Thr Glu Ala
            340

<210> SEQ ID NO 3
<211> LENGTH: 354
<212> TYPE: PRT
<213> ORGANISM: Microbacterium sp. MA1

<400> SEQUENCE: 3

Met Thr Asn Ile Arg Ala Val Val Tyr Gly Val Gly Ala Met Asn Ser
1               5                   10                  15

Val Ile Thr Arg Tyr Leu Leu Asp Lys Asp Val Glu Ile Val Gly Ala
            20                  25                  30

Ile Ser Arg Ser Pro Asp Lys Val Gly Lys Asp Leu Gly Glu Val Thr
        35                  40                  45

Gly Leu Asp Arg Arg Leu Gly Val Ser Ile Ser Asp Asp Pro His Glu
    50                  55                  60

Val Phe Thr Arg Thr Ser Pro Asp Ile Ala Val Val Ala Ile Thr Ser
65                  70                  75                  80

Tyr Leu Val Asp Ala Ala Glu His Phe Arg Ile Ala Leu Ser His Gly
                85                  90                  95

Val Asn Val Ile Thr Leu Ser Glu Glu Ala Leu Tyr Pro Trp Asn Thr
            100                 105                 110

Ala Pro Glu Leu Thr Ala Glu Leu Asp Ala Leu Ala Lys Glu His Gly
            115                 120                 125

Val Thr Ile Thr Gly Gly Phe Gln Asp Ser Phe Trp Val Asn Ala
        130                 135                 140

Val Ala Gln Leu Met Gly Thr Ala His Arg Ile Asp Ser Val Thr Gly
145                 150                 155                 160

Thr Ser Ser Trp Asn Val Asp Glu Tyr Gly Pro Glu Leu Ala Glu Leu
```

```
                    165                 170                 175
Gln Gln Val Gly Ala Thr Ile Glu Glu Phe Asp Ala Trp Cys Arg Glu
            180                 185                 190
Ala Val Arg Pro Pro Thr Phe Gly Arg Ile Ala Leu Asp Ala Leu Val
        195                 200                 205
Ala Gly Ala Gly Leu Thr Pro Lys Gln Ile Leu Thr Arg Thr Glu Pro
    210                 215                 220
Glu Leu Ala His Glu Thr Leu His Cys Ala Ala Leu Gly Ile Asp Val
225                 230                 235                 240
Pro Pro Gly Lys Cys Ile Gly Phe Thr Asp Ile Asp Glu Ile Arg Thr
                245                 250                 255
Glu Glu Gly Pro Val Phe Val Phe Arg Met Ser Gly Arg Leu Tyr Gly
            260                 265                 270
Pro Asp Asp Ser Asp Val Asn Glu Trp Thr Ile His Gly Glu Pro Asp
        275                 280                 285
Leu Val Met Ser Asn Gly Thr Pro Pro Thr Met Ala Thr Thr Cys Thr
    290                 295                 300
Gln Leu Val Asn Arg Ile Pro Asp Val Leu Ala Asp Pro Gly Phe
305                 310                 315                 320
Val Thr Val Val Asp Leu Pro Arg Leu Arg Tyr Arg His Gly Arg Leu
                325                 330                 335
His Asp His Leu Ser Arg Trp Ser Asp Arg Tyr Ile Val Arg Glu
            340                 345                 350
Glu Leu

<210> SEQ ID NO 4
<211> LENGTH: 341
<212> TYPE: PRT
<213> ORGANISM: Aminomonas paucivorans DSM 12260

<400> SEQUENCE: 4

Met Glu Lys Ile Arg Val Ile Gln Tyr Gly Cys Gly Lys Met Gly Lys
1               5                   10                  15
Val Phe Leu Arg Tyr Leu His Glu Lys Gly Ala Glu Ile Val Gly Ala
            20                  25                  30
Ile Asp Gly Asn Pro Glu Leu Glu Gly Lys Asp Ala Gly Glu Val Ala
        35                  40                  45
Gly Leu Gly Phe Lys Leu Asn Val Pro Val His Thr Asp Ala Asp Ser
    50                  55                  60
Val Phe Glu Ser Cys Asp Ala Asp Ala Cys Ile Ile Ala Val Ala Ser
65                  70                  75                  80
Leu Met Glu Asp Met Leu Pro His Leu Glu Arg Ala Ala Arg Tyr Gly
                85                  90                  95
Val Asn Ala Ile Thr Thr Cys Glu Glu Ala Phe Tyr Pro Trp Thr Thr
            100                 105                 110
Ser Pro Ala Ile Thr Asn Arg Leu Asp Arg Leu Ala Lys Glu Thr Gly
        115                 120                 125
Cys Thr Leu Ala Gly Ser Gly Tyr Gln Asp Val Phe Trp Gly Asn Leu
    130                 135                 140
Ile Ser Val Leu Ala Gly Ala Thr His Arg Ile Asp Arg Ile Glu Gly
145                 150                 155                 160
Val Thr Ser Tyr Asn Val Glu Asp Tyr Gly Ile Ala Leu Ala Lys Val
                165                 170                 175
His Gly Ala Gly Leu Ser Lys Glu Asp Phe Arg Arg Glu Ile Ala Glu
```

```
                180             185                 190
Asn Asp Ser Leu Pro Ser Tyr Val Trp Asn Ser Asn Glu Trp Leu Cys
            195                 200                 205

Ser Gln Met Gly Trp Thr Ile Lys Gly Met Lys Gln Glu Leu Val Pro
            210                 215                 220

Thr Phe His Asp Val Pro Leu Lys Ser Glu Thr Leu Gly Thr Thr Ile
225                 230                 235                 240

Pro Ala Gly His Ala Thr Gly Met Ser Ala Val Val Thr Thr Glu Thr
                245                 250                 255

Tyr Gln Gly Pro Val Ile Val Thr Gln Cys Ile Gly Lys Val Tyr Ala
            260                 265                 270

Pro Gly Glu Val Asp Arg Asn Asp Trp Val Leu Lys Gly Glu Pro Asn
            275                 280                 285

Thr Thr Val Gln Ile Ala Cys Pro Ala Thr Val Glu Leu Thr Cys Ala
            290                 295                 300

Thr Leu Val Asn Arg Leu Pro Asp Leu Leu Ser Pro Ala Gly Phe
305                 310                 315                 320

Phe Thr Thr Glu Lys Met Pro Ala Ala Ala Tyr Arg Thr Tyr Pro Leu
                325                 330                 335

His Leu Tyr Val Arg
            340

<210> SEQ ID NO 5
<211> LENGTH: 337
<212> TYPE: PRT
<213> ORGANISM: Mycobacterium vaccae ATCC 25954

<400> SEQUENCE: 5

Met Gln Met Ser Gly Val Arg Ala Val Val Tyr Gly Val Gly Ala Met
1               5                   10                  15

Asn Ser Ile Ile Ala Gly Met Leu Ile Asp Lys Gly Val Glu Ile Val
            20                  25                  30

Gly Ala Ile Ala Arg Ser Pro Gln Lys Val Gly Gln Asp Leu Gly Asp
        35                  40                  45

Val Ile Gly Phe Gly Arg Gln Leu Gly Val Thr Val Ser Asp Asp Ala
    50                  55                  60

Ala Ala Val Phe Ala Gln Thr Arg Pro Asp Val Ala Val Ile Ala Val
65                  70                  75                  80

Asn Ser Tyr Leu Thr Asp Ala Val Glu Gln Leu Arg Ile Cys Ala Glu
                85                  90                  95

His Gly Val Asn Ala Val Thr Leu Ser Glu Glu Met Leu Tyr Pro Trp
            100                 105                 110

Glu Thr Ser Pro Glu Leu Ala Ala Glu Leu Asp Ala Leu Ala Lys Ser
            115                 120                 125

Thr Gly Ala Thr Leu Thr Gly Thr Gly Phe Gln Asp Thr Phe Trp Val
        130                 135                 140

Asn Ile Val Ala Leu Leu Met Gly Thr Ala His Arg Ile Asp Thr Val
145                 150                 155                 160

Cys Gly Lys Ala Ser Trp Asn Val Asp Asp Phe Gly Pro Glu Leu Ala
                165                 170                 175

Thr Ala Gln Gln Val Gly Arg Ala Val Ala Glu Phe Glu Glu Trp Val
            180                 185                 190

Arg Gly Ala Gln Arg Pro Pro Thr Phe Gly Arg Asn Val Leu Asp Ala
            195                 200                 205
```

Leu Val Ala Asp Thr Gly Leu Thr Val Ser Ser Ile Ser Thr Thr Thr
210                 215                 220

Arg Pro Asp Ile Ala Phe Ala Met Arg Ser Glu Ala Leu Gly Ile
225                 230                 235                 240

Asp Leu Ala Pro Gly Asp Val Val Gly Phe Thr Asp Ile Asp Arg Ile
                    245                 250                 255

Glu Thr Ala Glu Gly Pro Ala Phe Val Phe Glu Met Ser Gly Arg Val
                260                 265                 270

Tyr Gly Thr Gly Glu Gly Asp Ile Asn Glu Trp Thr Ile Glu Gly Glu
                275                 280                 285

Pro Asn Leu Phe Leu Ser Asn Gly Thr Val Pro Thr Gln Thr Thr Thr
290                 295                 300

Cys Thr Gln Leu Val Asn Arg Ile Pro Asp Val Ile Ala Ala Pro Pro
305                 310                 315                 320

Gly Ile Val Thr Val Asp Lys Leu Pro Arg Leu Arg Tyr Arg Thr Arg
                    325                 330                 335

Phe

<210> SEQ ID NO 6
<211> LENGTH: 343
<212> TYPE: PRT
<213> ORGANISM: Mycobacterium sp. GA-2829

<400> SEQUENCE: 6

Met Gly Pro Ile Lys Ala Val Tyr Gly Val Gly Ala Met Asn Ser
1               5                   10                  15

Ile Ala Thr Arg Met Leu Leu Asp Lys Gly Val Glu Val Val Gly Ala
                20                  25                  30

Ile Ala Arg Ser Glu Ala Lys Val Gly Arg Asp Leu Gly Glu Val Ala
            35                  40                  45

Gly Leu Gly Arg Glu Leu Gly Val Ala Val Ser Gly Asp Ala Ala Glu
50                  55                  60

Val Phe Arg Arg Thr Ser Pro Asp Val Ala Val Ile Ala Val Asn Ser
65                  70                  75                  80

Tyr Leu Ala Asp Ala Val Glu Gln Leu Arg Ile Cys Ala Glu His Gly
                85                  90                  95

Val Asn Ala Val Thr Leu Ser Glu Glu Met Leu Tyr Pro Trp Asn Thr
            100                 105                 110

Ser Pro Gly Leu Ala Glu Glu Leu Asp Ala Ala Lys Arg Thr Gly
        115                 120                 125

Val Thr Leu Thr Gly Thr Gly Phe Gln Asp Thr Phe Trp Val Asn Gln
    130                 135                 140

Ile Ala Leu Leu Met Gly Thr Val His Arg Ile Asp Ser Val Ser Gly
145                 150                 155                 160

Arg Ala Ser Trp Asn Val Asp Asp Phe Gly Pro Glu Leu Ala Arg Asp
                165                 170                 175

Gln Gln Val Gly Cys Ser Val Ala Glu Phe His Asp Trp Leu Arg Asp
            180                 185                 190

Ala Glu Arg Pro Pro Thr Phe Gly Arg Asn Val Leu Asp Ala Leu Ile
        195                 200                 205

Ala Asp Thr Gly Leu Thr Pro Thr Ser Val Thr Ser Thr Thr Arg Pro
    210                 215                 220

Asp Val Ala Ala Ala Pro Met Phe Ser Gln Ala Leu Gln Ile Glu Val
225                 230                 235                 240

Pro Ala Gly Ser Val Ile Gly Ile Thr Asp Val Asp Glu Ile Lys Thr
            245                 250                 255

Glu Gln Gly Pro Ser Phe Leu Phe Glu Met Ser Gly Arg Val Tyr Gly
        260                 265                 270

Val Asp Glu Gly Asp Ile Asn Glu Trp Glu Ile Ser Gly Glu Pro Asp
    275                 280                 285

Val Val Leu Ser Asn Gly Thr Val Pro Thr Gln Leu Thr Thr Cys Thr
290                 295                 300

Gln Leu Val Asn Arg Ile Pro Asp Val Ile Ala Arg Pro Gly Ile
305                 310                 315                 320

Ile Thr Val Asp Glu Leu Ala Arg Leu Arg Tyr Arg Ala Phe Pro Leu
            325                 330                 335

His Thr Tyr Leu Arg Gly Ala
            340

<210> SEQ ID NO 7
<211> LENGTH: 1008
<212> TYPE: DNA
<213> ORGANISM: Artificial
<220> FEATURE:
<223> OTHER INFORMATION: ADNc of SEQ ID NO:1

<400> SEQUENCE: 7

```
atgtccgata ttcgggccgt ggtatacggc gttggcgcga tgaactcgat cgtcgccggc      60
atgctgctcg acaaaggggt gcagatcgtc ggggcgatcg cacgcagccc acaaaaggtc     120
gggcaggacc tcggcgacct gctcggtctg gccggcaac tcggcgtcgc ggtgagcgac      180
gacgccgcgg aggtgctcga gcagacccac cccgacatcg cggtgatcgc ggtcaacagc    240
tacctcaccg atgccgtcga acagttgcgg atctgcgccg agcacggggt caacgccgtc    300
acgctgtccg aagagatgct ctacccgtgg gagacctcgc ccgaactgtc cgccgagttg    360
gatgccctgg ccaagtcgac cggcgcgacc ttgacgggga ccggatacca ggacaccttc    420
tgggtcaaca tgatcgccct gctcatgggc accgcccacc ggatcgacac cgtccgcggc    480
aaggcgagtt ggaacgtcga cgacttcggc cccgaactgg ccaccgcgca gcaggtggga    540
cggaccgtcg ccgagttcga cgagtgggtc cgcggggccc agcggccgcc gaccttcggt    600
cgcaacgtgc tcgacgccct ggtcgccgac accggtctga ccgtcaaatc gatcaccacc    660
gccacccgtc cggacatcgc ctctgcggca atgcgttccg aggccctcgg tatcgacctg    720
gcaccagggg acgtgatcgg attcaccgat atcgaccgga tcgagaccga gagggaccg    780
gtgttcgagt cgagatgtc gggtcgggtg tacggacccg tgagggtga catcaacgag     840
tggacgatcg agggcgagcc gaacctgttc ctgtccaacg gaaccgtgcc gacccagacc    900
accacctgca cccagatggt gaaccggatt cccgacgtga ttgccgcgcc gcccggcatc    960
gtcaccgtcg acaggcttcc tcgactgcgt tatcgacccc agttctga             1008
```

<210> SEQ ID NO 8
<211> LENGTH: 1029
<212> TYPE: DNA
<213> ORGANISM: Artificial
<220> FEATURE:
<223> OTHER INFORMATION: ADNc of SEQ ID NO:2

<400> SEQUENCE: 8

```
atgagcaaga gaccgatccg gatcatccag tggggttgcg gcttgatggg tcagaccctc      60
atccgtaccc tgcgcgagaa gggcgccgaa ctggtggggg ccatcgatca acgcggcc      120
```

| | |
|---|---|
| cgccgggacc gggatgcggg agaggtggcc gggctcggcc agtcgctcgg cgtgcgcatc | 180 |
| caccctcccg atcaggccga tgccgtcttc cgtgaggccc gggccgacgt gtgcatcctg | 240 |
| tgcacgcgca gcatcatgag cgagctggcc ggcgccctgc gcgtggccgc ccgtcacggc | 300 |
| gtcaacgcca tcaccatcgg agaggaggcg ttctatccgt ggacgacttc ccaggcgctc | 360 |
| accgaggagt tggaccagct ggccagggcc aacgactgca ccctcaccgg ctcgggcttc | 420 |
| caggacgtgt tctggggcaa cctcatcacc gtgctggccg cgccacccca ccgcatcgat | 480 |
| cgcatcgtgg ggctgaccca gtacaacgcg gatgactacg ggagcgcgct ggcgcagaag | 540 |
| catggcgtcg gactcgatcc ggagaccttc gcggccagga ttggcgccag caactcaccc | 600 |
| tcctacgtct ggaactccaa cgagtggctg tgcgcccagc tcggctggcg tgtgcgagac | 660 |
| atccgccagc aactgctgcc caccacccat accgggacgc tgcgctcggc gagcctcggc | 720 |
| cgtgaggttc ccgccgggca tgccacgggc atgaaggcgg tggtggtgac ggagacgcac | 780 |
| gagggcccgg tcatcgagac gcactgcgtg ggcaagctct acgcgcccgg cgaggtagac | 840 |
| ctcaacgagt ggacgctgcg gggcgagccc gacaccacgg tgaccatccg ccagccggcg | 900 |
| acgcccgcgc tcacgtgcgc caccgtgctc aaccgtctgc ccaactgct ggccgcgccc | 960 |
| ccgggcttcg tcaccaccga ccgcttcacg cccgccacct atgtctcccg cctggagacg | 1020 |
| gaggcgtaa | 1029 |

<210> SEQ ID NO 9
<211> LENGTH: 1065
<212> TYPE: DNA
<213> ORGANISM: Artificial
<220> FEATURE:
<223> OTHER INFORMATION: ADNc of SEQ ID NO:3

<400> SEQUENCE: 9

| | |
|---|---|
| atgacgaaca tcagagctgt cgtgtacggc gtcggagcga tgaactccgt gatcacccgc | 60 |
| tatctgctcg acaaggacgt cgagatcgta ggcgccatct cgcgcagtcc ggacaaggtg | 120 |
| ggcaaggacc tcggcgaggt caccggactc gaccgtcgac tcggagtgtc gatcagcgac | 180 |
| gacccgcacg aggtgttcac gcggacgagt cccgacatcg cggtcgtcgc gatcaccagc | 240 |
| tatctcgtgg acgccgcgga gcacttccgt atcgcactgt cgcacggggt caacgtgatc | 300 |
| acgctgtccg aggaagcgct ctatccctgg aacaccgcgc ccgaactgac cgcggaactc | 360 |
| gatgcactcg ccaaggagca tggcgtgacc atcacgggcg ggggtttcca ggacagcttc | 420 |
| tgggtgaacg cggtcgccca gctgatgggc acggcacacc gcatcgactc ggtcaccggg | 480 |
| acgagttcgt ggaacgtcga cgagtacggc ccggaactgg ccgagctgca gcaggtcggc | 540 |
| gcgacgatcg aggagttcga cgcctggtgc gagaagccg tgcgtccgcc cacattcggc | 600 |
| cggatcgctc tcgatgcgct ggtcgccgga gcggggctga cgcccaagca gatcctgacg | 660 |
| cgcaccgaac ccgaactggc acacgagact ctgcactgtg ctgccctggg gatcgacgtc | 720 |
| ccgccgggaa agtgcatcgg cttcaccgac atcgacgaga tccgcacgga gagggcccg | 780 |
| gtcttcgtct tccggatgtc cggccggctg tacggccccg acgacagcga tgtcaacgaa | 840 |
| tggacgatcc acgcgaacc cgatctggtg atgtccaacg gcaccccgcc gacgatggcc | 900 |
| accacctgca cccaattggt gaaccgtatc cccgacgtgc tcgacgccga cccgggattc | 960 |
| gtgaccgtcg tcgatctgcc caggctgcgc taccggcacg tcggctgca cgaccacctg | 1020 |
| agcaggtggt catcggatcg ttacatcgtg cgcgaagaac tgtaa | 1065 |

<210> SEQ ID NO 10
<211> LENGTH: 1026
<212> TYPE: DNA
<213> ORGANISM: Artificial
<220> FEATURE:
<223> OTHER INFORMATION: ADNc of SEQ ID NO:4

<400> SEQUENCE: 10

```
atggagaaga tccgggtgat ccagtacggc tgcggcaaga tgggcaaggt cttcctgcgg      60
tacctgcacg agaagggcgc ggagatcgtg ggggccatcg acggcaaccc cgagctggag     120
ggcaaggacg ccggtgaggt ggcggggctg ggcttcaagc tgaacgtgcc ggtgcacacc     180
gacgcggact cggtgttcga gtcctgcgac gccgacgcct gcatcatcgc cgtggccagc     240
ctcatggagg acatgctccc ccacctggag cgggcggccc gctacggggt gaacgccatc     300
accacctgcg aggaggcctt ctacccttgg accacctccc ccgccatcac caaccggctg     360
gaccggctgg ccaaggagac ggggtgcact ctggcgggat cgggctacca ggacgtgttc     420
tggggcaacc tgatctccgt gctggcgggg gccacccacc gcatcgaccg catcgagggg     480
gtcaccagct acaacgtgga ggactacggc atcgccctgg cgaaggtcca cggagcgggg     540
ctgagcaagg aggacttccg cagggagatc gcggagaacg actccctccc ctcctatgtg     600
tggaactcca acgagtggct ctgctcccag atgggctgga ccatcaaggg catgaaacag     660
gagctggtgc ccacgttcca cgacgtcccc ctgaagtccg agaccctggg gaccaccatc     720
cccgcagggc acgccacggg catgtccgcg gtggtcacca cggagaccta ccaggggccg     780
gtgatcgtca cccagtgcat cggcaaggtg tacgcccccg cgaggtggga ccggaacgac     840
tgggtcctca aggggagcc gaacaccacc gtccagatcg cctgccccgc cacggtggag     900
ctgacctgcg ccaccctggt gaaccgcctg ccggacctgc cctgtcccc cgcaggcttc     960
ttcaccaccg agaagatgcc cgccgcagcc taccgcacct atcctctgca cctctacgtc    1020
cgctga                                                                1026
```

<210> SEQ ID NO 11
<211> LENGTH: 1014
<212> TYPE: DNA
<213> ORGANISM: Artificial
<220> FEATURE:
<223> OTHER INFORMATION: ADNc of SEQ ID NO:5

<400> SEQUENCE: 11

```
atgcagatgt ccggcgtccg ggctgtggtg tatggagtcg cgcgatgaa ttcgatcatc       60
gccggcatgc tgatcgacaa gggggtggag atcgtcggtg cgatcgcccg cagcccgcag     120
aaggtcggac aggatctcgg tgacgtgatc ggattcggcc gtcagctcgg cgtcacggtc     180
agcgacgacg ccgcggcggt tttcgcgcag acccgaccgg atgtggcggt gatcgcggtg     240
aacagctacc tcaccgatgc cgttgaacag ctgcgcatct cgccgaaca cggagtcaac     300
gccgtcacgc tgtccgaaga gatgctctac ccgtgggaga cctcgcccga gctggccgcc     360
gagttggacg cgctggccaa gtccacgggg gcgaccctga ccgggacggg atttcaggac     420
accttctggg tgaacatcgt cgcgctgctg atgggtaccg cacaccggat cgacaccgtc     480
tgcggcaagg cgagttggaa cgtcgacgac ttcggtcccg aattggcgac ggctcaacag     540
gtgggtcgcg cggtcgcaga gttcgaggag tgggtccggg gtgcgcagcg ccctccgacc     600
tttggtcgca acgtgctcga tgcgctggtc gccgacaccg gctgaccgt cagctcgatc     660
agcaccacca ctagacccga catcgctttc gcggcaatgc gttcggaagc gctgggcatc     720
```

```
gacctcgcac ctggggacgt cgtgggattc accgatatcg accggatcga gaccgcggag    780
gggcccgcct tcgtcttcga gatgtcgggc cgggtgtacg ggaccggcga aggtgacatc    840
aacgagtgga ccatcgaagg cgagccgaac ctgttcctgt ccaacggaac cgtgcccaca    900
cagacgacca cgtgcaccca gctcgtgaac cggattcccg atgtgatcgc ggcaccgccg    960
ggcatcgtca ccgtcgacaa gctcccgcgc ctgcgctacc gcacgcgatt ctga         1014
```

<210> SEQ ID NO 12
<211> LENGTH: 1032
<212> TYPE: DNA
<213> ORGANISM: Artificial
<220> FEATURE:
<223> OTHER INFORMATION: ADNc of SEQ ID NO:12

<400> SEQUENCE: 12

```
atgggcccga tcaaggcggt cgtttacgga gtcggcgcga tgaactcgat cgcgacgcgc     60
atgctgctcg acaaggggt ggaggtggtc ggggccatcg cgcgcagcga agccaaggtc    120
ggccgcgatc tcggcgaggt cgccggcctc ggccgcgaac tcggcgtcgc cgtcagtggg    180
gatgcggccg aggtgtttcg ccggacgtcg ccggacgtgg ccgtcatcgc ggtcaacagc    240
tacctggcgg atgccgtgga gcaactacgc atctgcgccg aacacggcgt caacgcggtc    300
acgttgtccg aggagatgct ctatccctgg aacacctcgc ccggtctcgc cgaggaactc    360
gacgcggcgg ccaagcggac cggggtgacg ctgacgggca ccggcttcca ggacaccttc    420
tgggtgaacc agatcgccct gctgatgggc accgtgcatc gcatcgattc ggtgtcgggg    480
cgggcgagtt ggaacgtcga cgacttcgga cccgagctgg cgcgcgacca acaggtcggc    540
tgttcggtgg ccgagttcca cgactggctg cgcgacgccg aacgtccacc caccttcggc    600
cgcaacgttc tcgacgcgtt gatcgcagac accgggttga cgccgacgtc ggtgacgtcg    660
acgacgcgtc cggatgtcgc tgcggccccg atgttctcgc aggcactgca gatcgaggtc    720
cccgcgggca gtgtcatagg gatcaccgat gtcgacgaga tcaagaccga gcagggaccc    780
agcttcctgt tcgagatgtc ggggcgcgtc tacggcgtcg acgaggggga catcaacgag    840
tgggagatct ccggtgagcc ggatgtggtg ctctccaacg gcacggtccc gacccagctg    900
accacctgca cccagctcgt caaccgcatc ccggatgtga tcgctgcgcg cccggggatc    960
atcaccgtcg acgagctggc ccgtctccga taccgcgcct tcccgctgca cacctacctg   1020
cggggtgcct ga                                                       1032
```